(12) United States Patent
Shekhar et al.

(10) Patent No.: US 11,344,180 B2
(45) Date of Patent: May 31, 2022

(54) SYSTEM, APPARATUS, AND METHOD FOR CALIBRATING OBLIQUE-VIEWING RIGID ENDOSCOPE

(71) Applicant: CHILDREN'S NATIONAL MEDICAL CENTER, Washington, DC (US)

(72) Inventors: Raj Shekhar, Washington, DC (US); Xinyang Liu, Washington, DC (US)

(73) Assignee: CHILDREN'S NATIONAL MEDICAL CENTER, Washington, DC (US)

(*) Notice: Subject to any disclaimer, the term of this patent is extended or adjusted under 35 U.S.C. 154(b) by 76 days.

(21) Appl. No.: 16/621,917

(22) PCT Filed: Jun. 15, 2018

(86) PCT No.: PCT/US2018/037881
§ 371 (c)(1),
(2) Date: Dec. 12, 2019

(87) PCT Pub. No.: WO2018/232322
PCT Pub. Date: Dec. 20, 2018

(65) Prior Publication Data
US 2021/0145254 A1 May 20, 2021

Related U.S. Application Data

(60) Provisional application No. 62/520,289, filed on Jun. 15, 2017.

(51) Int. Cl.
*A61B 1/00* (2006.01)
*A61B 1/05* (2006.01)
*A61B 5/06* (2006.01)

(52) U.S. Cl.
CPC ...... *A61B 1/00057* (2013.01); *A61B 1/00179* (2013.01); *A61B 1/05* (2013.01); *A61B 5/065* (2013.01)

(58) Field of Classification Search
CPC ... A61B 1/00057; A61B 1/00179; A61B 1/05; A61B 5/065; A61B 5/07; A61B 5/42;
(Continued)

(56) References Cited

U.S. PATENT DOCUMENTS 7,892,165 B2 * 2/2011 Nakamura ............ A61B 5/062
600/117
2001/0020937 A1 9/2001 Rosenberg et al.
(Continued)

OTHER PUBLICATIONS

Wu, C., B. Jaramaz, and S. G. Narasimhan. "A full geometric and photometric calibration method for oblique-viewing endoscopes." Computer Aided Surgery 15.1-3 (2010): 19-31.*
(Continued)

*Primary Examiner* — Timothy J Neal
*Assistant Examiner* — Sung Ham
(74) *Attorney, Agent, or Firm* — Oblon, McClelland, Maier & Neustadt, L.L.P.

(57) ABSTRACT

The present disclosure relates to an apparatus and method for correcting rotational error during use of an oblique-viewing endoscope. Specifically, the present disclosure relates to a fast calibration process wherein a new approach is employed in estimating a center of rotation of a plane of an image. Moreover, the approach, allows for updating of a camera matrix during use.

20 Claims, 13 Drawing Sheets

(58) Field of Classification Search
CPC ............ A61B 2560/0223; A61B 5/062; G02B 23/2453; G02B 23/2476
USPC ........................................................ 600/171
See application file for complete search history.

(56) References Cited

U.S. PATENT DOCUMENTS

| | | | |
|---|---|---|---|
| 2001/0051761 A1 | 12/2001 | Khadem | |
| 2014/0028819 A1* | 1/2014 | Nakano | A61B 1/00009 348/65 |
| 2014/0285676 A1* | 9/2014 | Barreto | H04N 17/002 348/187 |
| 2015/0173723 A1* | 6/2015 | Bates | A61B 8/58 600/424 |

OTHER PUBLICATIONS

Liu, Xinyang, et al. "On-demand calibration and evaluation for electromagnetically tracked laparoscope in augmented reality visualization." International journal of computer assisted radiology and surgery 11.6 (2016): 1163-1171.*

International Search Report and Written Opinion dated Aug. 31, 2018 in PCT/US2018/037881 filed on Jun. 15, 2018.

* cited by examiner

SYSTEM, APPARATUS, AND METHOD FOR CALIBRATING OBLIQUE-VIEWING RIGID ENDOSCOPE

CROSS-REFERENCE TO RELATED APPLICATIONS

The present application claims priority to U.S. Provisional Application No. 62/520,289, filed Jun. 15, 2017, the teaching of which is hereby incorporated by reference in its entirety for all purposes.

GOVERNMENT LICENSE RIGHTS

This invention was made with government support under 1R41CA192504 awarded by the National Institutes of Health (NIH). The government may have certain rights in the invention.

STATEMENT REGARDING PRIOR DISCLOSURE BY THE INVENTORS

Aspects of this technology are described in an article "Fast calibration of electromagnetically tracked oblique-viewing rigid endoscopes", published in International Journal of Computer Assisted Radiology and Surgery, on Jun. 16, 2017, which is incorporated herein by reference in its entirety.

BACKGROUND

Field of the Disclosure

The present disclosure relates to a calibration of oblique-viewing (i.e. angled) rigid endoscopes, including systems, apparatuses, and methods thereof.

Description of the Related Art

Computer-assisted surgery, based on the development of an accurate digital model of a patient, is an increasingly integral component of modern patient care. The implementation and expansion of computer-assisted surgery approaches to endoscopy requires accurate calibration of a rigid endoscope, a process including camera calibration and hand-eye calibration. In calibration of the camera, intrinsic parameters (e.g., focal length, principal point) and distortion coefficients of the camera can be determined. To the same end, hand-eye calibration, a concept borrowed from robotics, provides a rigid transformation between a coordinate system of the camera lens and a coordinate system of the tracking device attached to the camera.

Rigid endoscope calibration may be beneficial or even critical to many computer-assisted surgery applications, including emerging applications of augmented reality. In augmented reality, virtual models or tomographic images may be overlaid on live endoscopic video to enhance intraoperative visualization. In order to achieve this, augmented reality systems often rely on tracking techniques including optical tracking. The accuracy and speed of these tracking techniques become important in the context of rigid endoscopes, and oblique-viewing rigid endoscopes, specifically. Oblique—viewing rigid endoscopes, having an angled lens relative to a camera, are of interest as they provide a larger field of view through rotation of its telescope than comparable forward-viewing, or relatively flat, rigid endoscopes. This angle, however, considering the relative rotation of the telescope and an accompanying camera, can create a rotational offset between the actual object shown in the camera image and the projected object obtained using calibration parameters established before rotation. An approach for correcting this rotational offset while providing the benefits of oblique-viewing rigid endoscopes has yet to be developed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a system and method for calibration of a rigid endoscope.

According to an embodiment, the present disclosure is related to a system for performing a calibration operation, comprising a rigid endoscope, including a telescope, a camera head having a camera and being rotatably coupled to the telescope, one or more spatial-tracking sensors, and a processing circuitry configured to obtain a rotation center of a first one of the one or more spatial-tracking sensors, the first one of the one or more spatial-tracking sensors being disposed on the telescope of the rigid endoscope, the telescope of the rigid endoscope being in a first pose, obtain a first calibration, the first calibration being related to the first pose, rotate, to a second pose, the telescope of the rigid endoscope relative to the camera head of the rigid endoscope, obtain a second calibration, the second calibration being related to the second pose, and select from the first calibration and the second calibration based upon a comparison of an error value between the first calibration and the second calibration, wherein a second one of the one or more spatial-tracking sensors is disposed on the camera head, and wherein the rotation of the telescope of the rigid endoscope relative to the camera head of the rigid endoscope is based upon a relative position of the first one of the one or more spatial-tracking sensors and the second one of the one or more spatial-tracking sensors.

According to an embodiment, the present disclosure is further related to a method of performing a calibration operation, comprising obtaining, via processing circuitry, a rotation center of a first one of one or more spatial-tracking sensors, the first one of the one or more spatial-tracking sensors being disposed on a telescope of a rigid endoscope, the telescope of the rigid endoscope being in a first pose, obtaining, via the processing circuitry, a first calibration, the first calibration relating to the first pose, rotating, to a second pose, the telescope of the rigid endoscope relative to a camera head of the rigid endoscope, obtaining, via the processing circuitry, a second calibration, the second calibration relating to the second pose, and selecting, via the processing circuitry, from the first calibration and the second calibration based upon a comparison of an error value between the first calibration and the second calibration, wherein a second one of the one or more spatial-tracking sensors is disposed on the camera head of the rigid endoscope, and wherein the rotation of the telescope of the rigid endoscope relative to the camera head of the rigid endoscope is based upon a relative position of the first one of the one or more spatial-tracking sensors and the second one of the one or more spatial-tracking sensors.

According to an embodiment, the present disclosure is further related to a non-transitory computer-readable storage medium storing computer-readable instructions that, when executed by a computer having a processing circuitry, cause the computer to perform a calibration operation, the calibration operation comprising obtaining a rotation center of a first one of one or more spatial-tracking sensors, the first one of the one or more spatial-tracking sensors being disposed on a telescope of a rigid endoscope, the telescope of the rigid endoscope being in a first pose obtaining a first calibration, the first calibration relating to the first pose, obtaining a second calibration, the second calibration relating to a second pose, and selecting from the first calibration and the second calibration based upon a comparison of an error value between the first calibration and the second calibration, wherein the second pose is achieved by rotating the telescope of the rigid endoscope relative to a camera head of the rigid endoscope, wherein a second one of the one or more spatial-tracking sensors is disposed on the camera head of the rigid endoscope, and wherein the rotation of the telescope of the rigid endoscope relative to the camera head of the rigid endoscope is based upon a relative position of the first one of the one or more spatial-tracking sensors and the second one of the one or more spatial-tracking sensors.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Endoscopy, employing an endoscope, is a minimally-invasive real-time imaging modality in which a camera lens is inserted into the body of a patient for visual inspection of internal structures including the respiratory pathway and gastrointestinal system. Therefore, procedures that employ endoscopes, such as minimally-invasive laparoscopic procedures, allow users to visualize tissues inside a patient without unnecessary surgical intervention that may increase risks to the patient.

Figure 1:
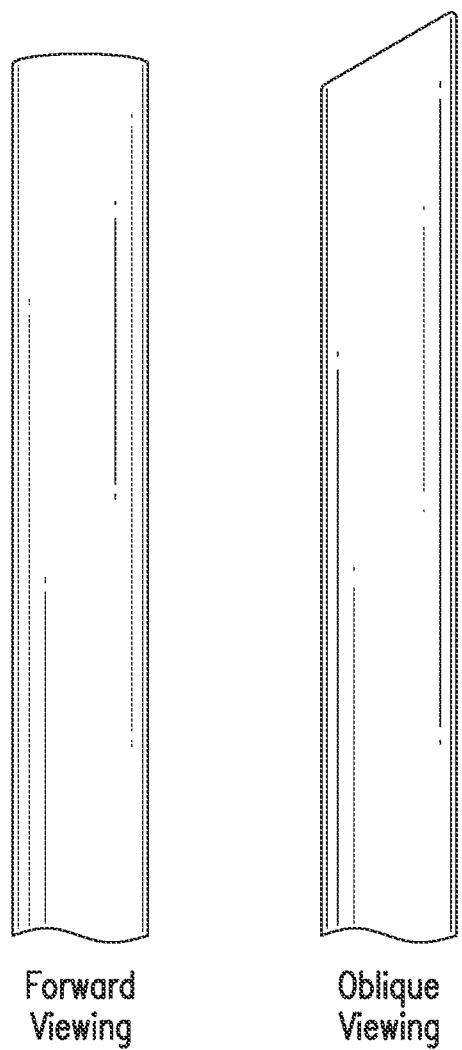
FIG. 1 is an illustration of a forward-viewing rigid endoscope and an oblique-viewing rigid endoscope, according to an exemplary embodiment of the present disclosure.
Figure 2:
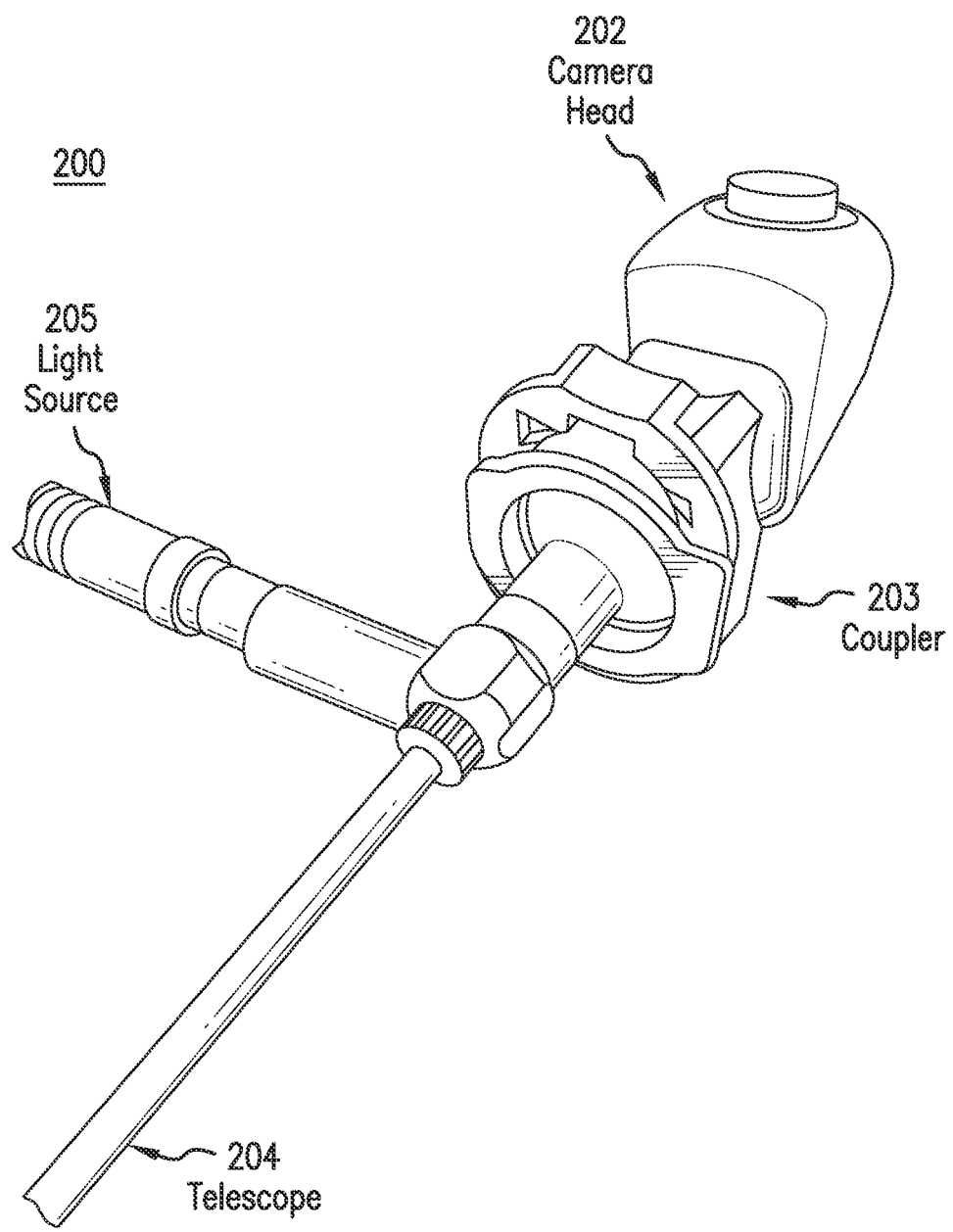
FIG. 2 is an illustration of an oblique-viewing rigid endoscope employed in a laparoscope, according to an exemplary embodiment of the present disclosure.

As minimally-invasive surgery becomes ubiquitous, and surgeons more heavily reliant thereupon, increasingly complex hardware and software need be developed to account for subtle yet impactful inaccuracies of current systems. One such inaccuracy stems from the inherent, and necessary, structure of rigid endoscopes. As shown in FIG. 1, an illustration of a distal end of a telescope of an endoscope, an endoscope may be a forward-viewing endoscope or an oblique-viewing endoscope, according to an embodiment of the present disclosure. Moreover, rigid endoscopes may comprise a camera head and a telescope, with a viewing lens, therein, rotatably coupled such that a user may adjust a field of view. In such cases, however, relative rotation of the two components of the endoscope can create significant errors in initial calibration parameters of the endoscope. FIG. 2 is an illustration of an endoscope in a laparoscopic system 200, wherein a telescope 204 and a light source 205 may be rotated about a long axis of the laparoscope 200 relative to a camera head 202, wherein the telescope 204 and the camera head 202 are coupled via a coupler 203.

The above-described calibration errors are especially critical with regard to surgical applications of augmented reality. Augmented reality, in the minimally-invasive surgical setting, promises to enhance intraoperative visualization. In an example, augmented reality methods may be used to integrate tomographic imaging data with intraoperative video to reveal internal anatomical structures, such as tumors, not ordinarily visible via intraoperative video. The resulting overlaid image allows a surgeon to visualize vasculature and other critical structures that may be below the visible surface of the operative area, and adjust a surgical plan, accordingly, in situ. This tool, fully implemented, may create a smart surgical visualization system that provides surgeons with greater confidence, minimizes complications, shortens procedure times, reduces blood loss, and helps expand the utilization of minimally-invasive techniques.

To this end, the present disclosure generally relates to systems, apparatuses, and methods for calibrating oblique-viewing rigid endoscopes in order to minimize calibration parameter inaccuracies. Moreover, the oblique-viewing rigid endoscope may be a spatially-tracked oblique-viewing rigid endoscope.

Specifically, according to an embodiment, the present disclosure relates to a calibration of an oblique-viewing rigid endoscope, for instance, using single-image calibration in order to compensate for a rotational offset between an actual object and a projection of an object due to a relative rotation between a telescope and a camera of the oblique-viewing rigid endoscope. The calibration may be an initial calibration and/or an update to the initial calibration, the update being performed after a relative rotation of components of the endoscope. The update can further comprise spatial-tracking of the relative rotation of the components of the oblique-viewing rigid endoscope. In an embodiment, the spatial-tracking may be performed via electromagnetic sensors disposed proximate to the components of the endoscope, the camera and the telescope, respectively. In another embodiment, the spatial-tracking may be performed via a combination of electromagnetic sensors and rotary encoders, wherein a rotary encoder is disposed proximate to the camera and an electromagnetic sensor is disposed proximate to the telescope.

Further, according to an embodiment, the present disclosure relates to an evaluation of the calibration accuracy, estimating a rotation center of a camera image, and updating a camera matrix in context of the direction of rotation.

The above-described systems, apparatuses, and methods may be implemented in a clinical setting and, therefore, may be a component of a computer-assisted surgical system, apparatus, or method. Implementations may, for instance, add two additional minutes to an existing clinical workflow, however, the calibration process can be performed in parallel to preparation of a computer-assisted surgery system employing an oblique-viewing rigid endoscope.

Spatial-Tracking

In addressing bulky and cumbersome optical tracking approaches of previous efforts, the present disclosure describes a tracking system for a conventional laparoscope employing an endoscope.

According to an embodiment, spatial-tracking of the relative rotation of the telescope and the camera head of the endoscope is critical to error correction. To this end, spatial-tracking sensors including but not limited to electromagnetic sensors and rotary encoders may be deployed.

In an embodiment, electromagnetic (EM) sensors, components of a spatial-tracking system, can be provided to, or as part of, an oblique-viewing rigid endoscope in order to report the location and orientation of a relatively small wired sensor inside a magnetic field created by a tabletop field generator. In an example, the oblique-viewing rigid endoscope may comprise a 30° 5-mm telescope. Further, the EM sensor may be as small as one millimeter in diameter.

In an embodiment, the tabletop field generator may be specifically designed for operating theater applications. The tabletop field generator may be positioned between a patient and a surgical table, within an operating theater, incorporating a shield suppressing distortions to the magnetic field introduced by metallic materials below the tabletop field generator.

According to an embodiment of the present disclosure, EM sensor spatial-tracking may be performed using one or more EM sensors, a first EM sensor mounted on a telescope of the oblique-view rigid endoscope and a second EM sensor mounted on a camera head of the oblique-view rigid endoscope. EM sensors and associated components of the oblique-viewing rigid endoscope, including a processing circuitry, may be configured to correct for EM sensor spatial-tracking errors. In an example, such correction includes but is not limited to minimizing, filtering, and compensating.

Figure 3:
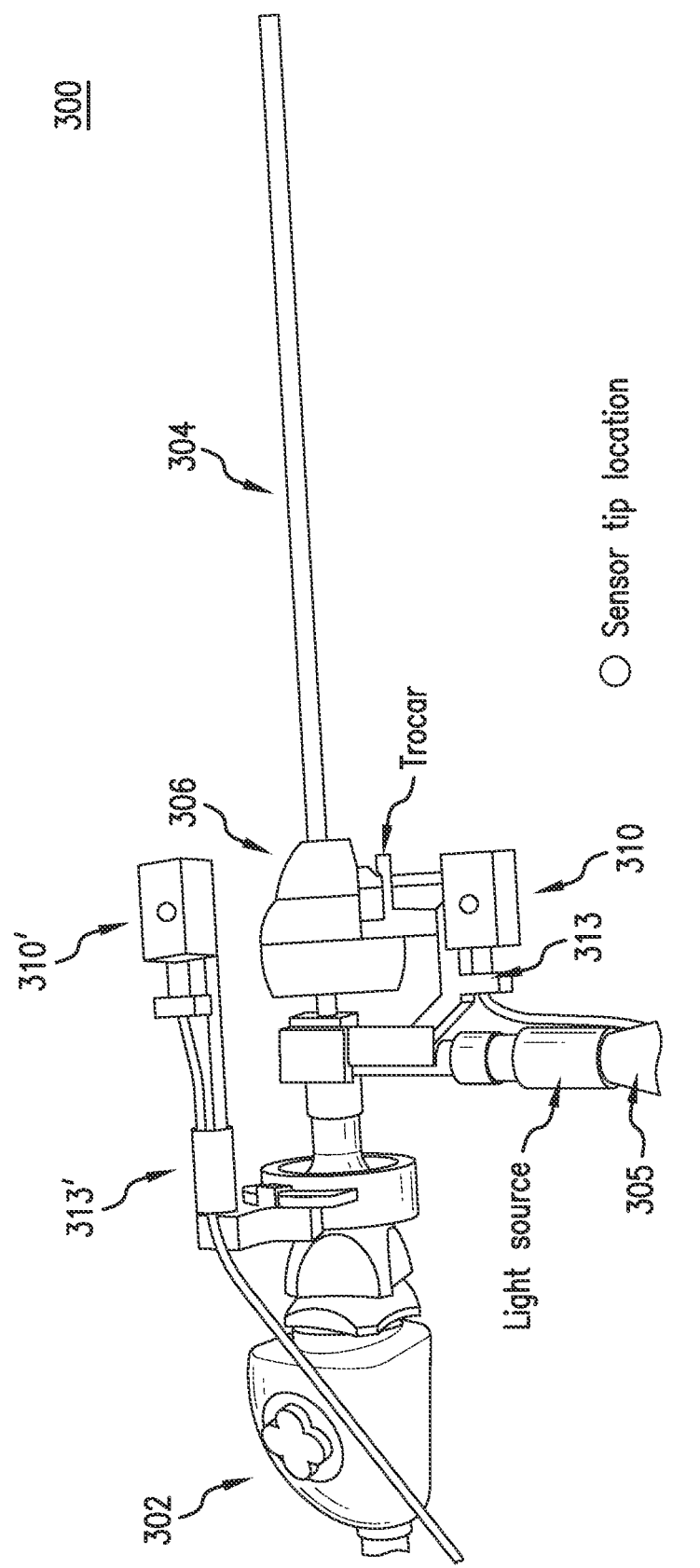
FIG. 3 is an illustration of an oblique-viewing rigid endoscope, comprising sensors, employed in a laparoscope, according to an exemplary embodiment of the present disclosure.

FIG. 3 is an illustration of an oblique-viewing rigid endoscope, according to an exemplary embodiment of the present disclosure. In an embodiment, the oblique-viewing rigid endoscope is a component of an oblique-viewing rigid laparoscope 300. The oblique-viewing laparoscope 300 comprises a telescope 304, a light source 305, a camera head 302, and a plurality of spatial-tracking sensors. According to an embodiment, the oblique-viewing rigid laparoscope 300, as shown in FIG. 3, is configured to be introduced to the body of a patient via a trocar 306. In an example, the plurality of spatial tracking sensors may be one or more EM sensors 310, 310'. The oblique-viewing rigid laparoscope 300 may comprise a 2D laparoscopic camera 302, for instance, with a 30° 5-mm telescope 304 fitted within a 5-mm trocar 306. Moreover, the one or more EM sensors 310, 310' may have 6 degrees-of-freedom and be configured to be detected within a magnetic field generated by a tabletop field generator.

As shown in FIG. 3, the one or more EM sensors 310, 310' may be coupled to the oblique-viewing rigid laparoscope 300 via one or more corresponding EM sensor mounts 313, 313'. The one or more EM sensor mounts 313, 313' may be fabricated via technique selected from a group including but not limited to injection molding, 3D printing, machining, or casting. Moreover, the one or more EM sensor mounts 313, 313' may be fabricated from a material selected from the group including but not limited to acrylonitrile butadiene styrene, polysulfone, polypropylene, polystyrene, polycarbonate, polyvinylchloride, synthetic fibers, or wood. In an embodiment, the one or more EM sensor mounts 313, 313' may be fixedly or removably coupled to the camera head 302 and the telescope 304 or light source 305, respectively. In an exemplary embodiment, each of the one or more EM sensor mounts 313, 313' are positioned at a remote distance from the camera head 302 so as to minimize distortion error of EM sensor spatial tracking introduced by the camera head 302.

While the above-described arrangement of the one or more EM sensor mounts 313, 313' may be appropriate for simulations, during clinical implementations of the EM sensor spatial-tracking system, the camera head 302 may be positioned above the lens of the telescope 304, relative to the patient. As a result, in these instances, the location of the one or more EM sensors 310, 310' may be proximate to the field generator without interacting with a tissue of the patient. In an embodiment, the one or more EM sensors 310, 310' and one or more EM sensor mounts 313, 313' may be sterilizable, minimizing safety issues with clinical use.

Compared with optical-based spatial-tracking approaches, the EM sensor spatial-tracking system of the present disclosure avoids issues related to a loss of line-of-sight and provides a greater possible range of rotation. In certain instances, however, the possible range of rotation may be limited to 326.5° due to physical constraints introduced by a relative position of a light source cable and one of the one or more EM sensor mounts 313 disposed on the camera head 302. Alternatively, in another embodiment, the EM sensor mount 313 disposed on the camera head 302 may be structurally modified such that no restriction is imposed on relative rotation of the telescope 304.

Clinical fCalib

According to an embodiment, and in order to accommodate oblique-viewing rigid endoscopes, a single-image calibration method has been incorporated in the calibration framework.

As alluded to above, and according to an embodiment, the present disclosure describes an implementation of a single-image calibration (SIC) to initialize and/or update calibration parameters. The SIC method, in an embodiment, may combine a SIC methodology estimating camera intrinsic parameters and distortion coefficients (e.g. P3D, Coimbra, Portugal) and hand-eye calibration so that a complete or more complete calibration can be achieved while minimizing the required number of calibration images. In an example, the SIC method of the present disclosure may require a single image of an arbitrary portion of a target pattern, as compared with multiple images required for comparable techniques.

The SIC method may be based on a clinical fCalib plate by laser-marking, for instance, a target, or calibration, pattern on a material. In an embodiment, the material for the calibration pattern may be selected from a group including but not limited to polyphenylsulfone, polysulfone, and polypropylene. In an example, the material may be a Radel® polyphenylsulfone, a type of heat and chemical resistant polymer. Moreover, the clinical fCalib calibration plate 415, shown in FIG. 4, can be sterilized via methods including but not limited to steam sterilization (e.g. autoclave), which may be beneficial for rapid oblique-viewing rigid endoscope calibration in an operating theater. Such calibration and evaluation methods associated with fCalib are understood in the art, as evidenced in the article by Liu et al. entitled "On-demand calibration and evaluation for electromagnetically tracked laparoscope in augmented reality visualization" published 2016 in International Journal of Computer Assisted Radiology and Surgery, which is incorporated herein by reference.

Figure 4:
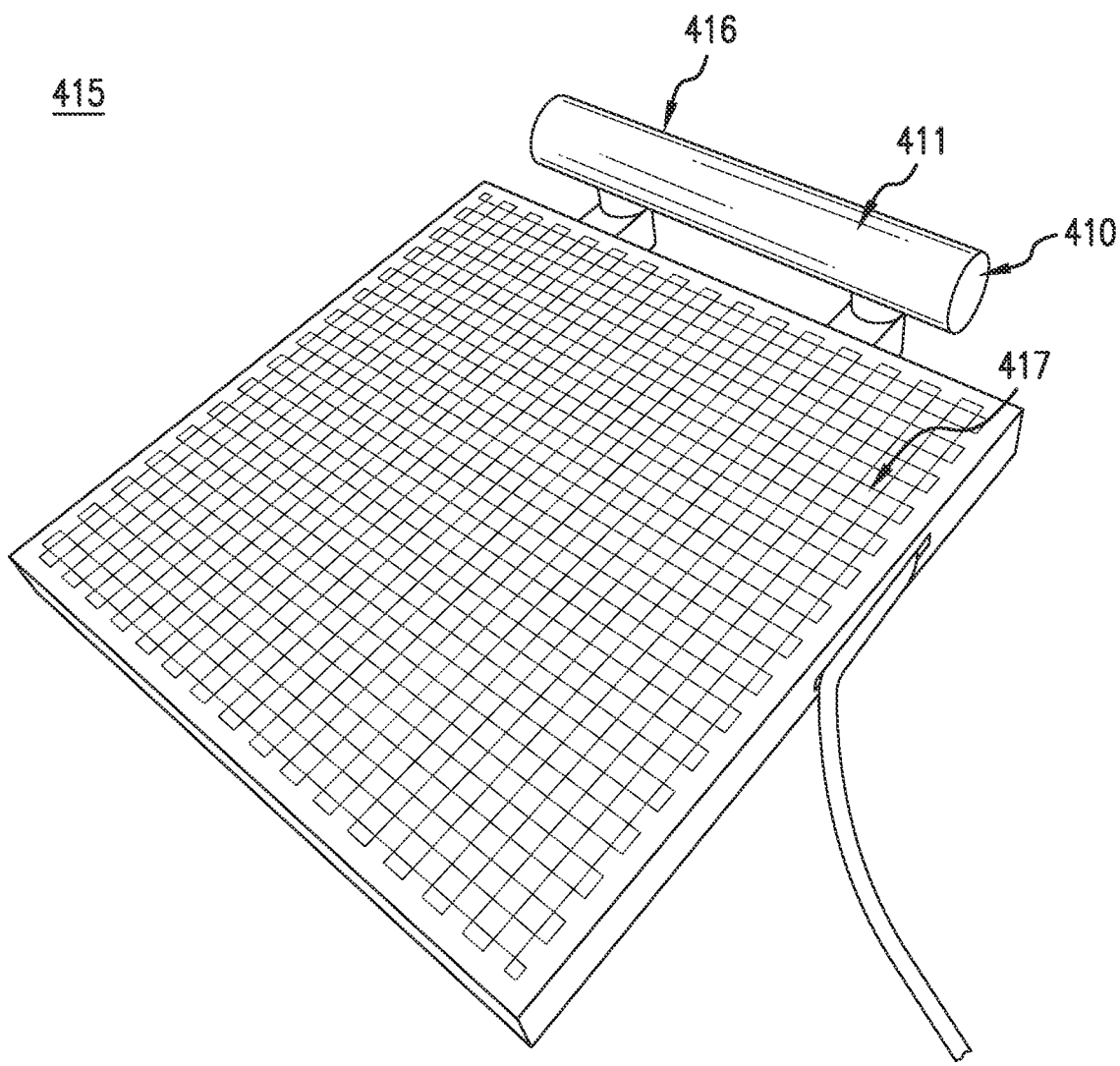
FIG. 4 is an illustration of a calibration plate, according to an exemplary embodiment of the present disclosure.

FIG. 4 is an illustration of a calibration plate of the above-described method, according to an exemplary embodiment of the present disclosure. The calibration plate 415 comprises a calibration pattern 417 and a tube phantom 416. A spatial-tracking sensor 410 may be disposed within the tube phantom 416. In an example, the spatial-tracking sensor 410 is an EM sensor 411 having six degrees-of-freedom. In an embodiment, the tube phantom 416 may be fixed on an aspect of the calibration plate 415 and registered with the spatial-tracking sensor 410 or, for instance, the EM sensor 411. In another embodiment, the calibration pattern 417 may comprise alternating black and white squares, each containing a unique marker, thereby making corner detection robust even in the case when partial images of the calibration pattern 417 are acquired. Further, the physical size of an edge of each square in the calibration pattern 417 may be 3.2 millimeters. According to an embodiment, registration defines a geometric relationship between the calibration pattern 417 and the EM sensor 411 of the tube phantom 416. In an embodiment, the geometric relationship between the calibration pattern 417 and the EM sensor 411 of the tube phantom 416 may fixed, thereby enabling laparoscopic calibration from a single image of the calibration plate 415 at an arbitrary angle.

According to an embodiment, the tube phantom 416 may be used for rapid visual evaluation of calibration accuracy. To this end, a virtual tube model, or for instance, a stack of rings, may be overlaid on the video image and a comparison with the actual tube in the video image may be made.

Therefore, according to an exemplary embodiment, due to hand-eye calibration and spatial-tracking for estimating a rotational center of a camera image, the present disclosure describes an approach applicable to augmented reality environments, wherein spatial-tracking is used to generate virtual models or tomographic images that may be overlaid with live endoscopic video to, for instance, enhance intraoperative visualization.

Calibration

According to an embodiment, wherein the telescope is stationary and only the camera head is rotated (this can be achieved by translation between coordinate systems according to (1), below), the camera image may rotate about a point in the image plane or, for instance, the rotation center in the image $O_{IMG}$.

$$p_{OM_1} = OM_{1_{TOT}} \cdot OM_{T_{OM_2}} \cdot p_{OM_2} \quad (1)$$

Figure 5B:
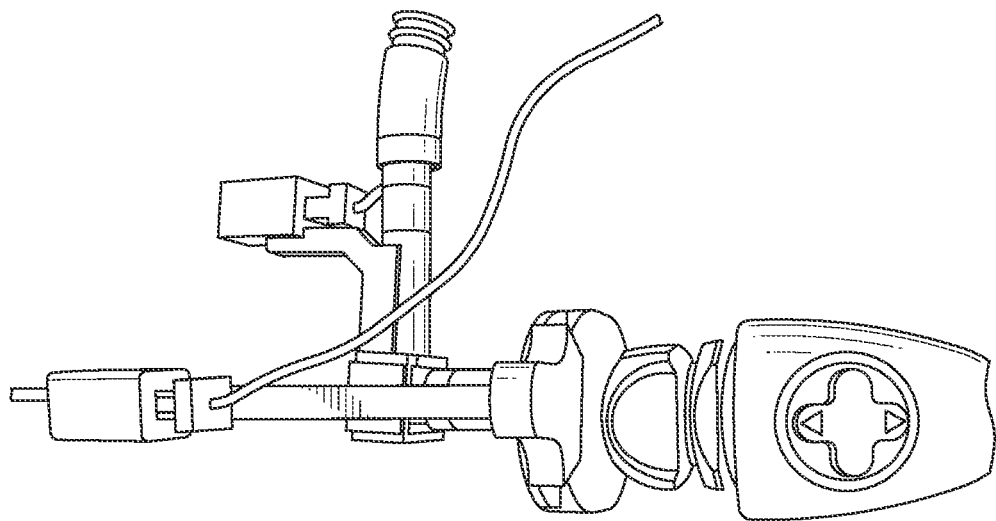
FIG. 5B is an illustration of an orientation of a laparoscope, according to an exemplary embodiment of the present disclosure.
Figure 5A:
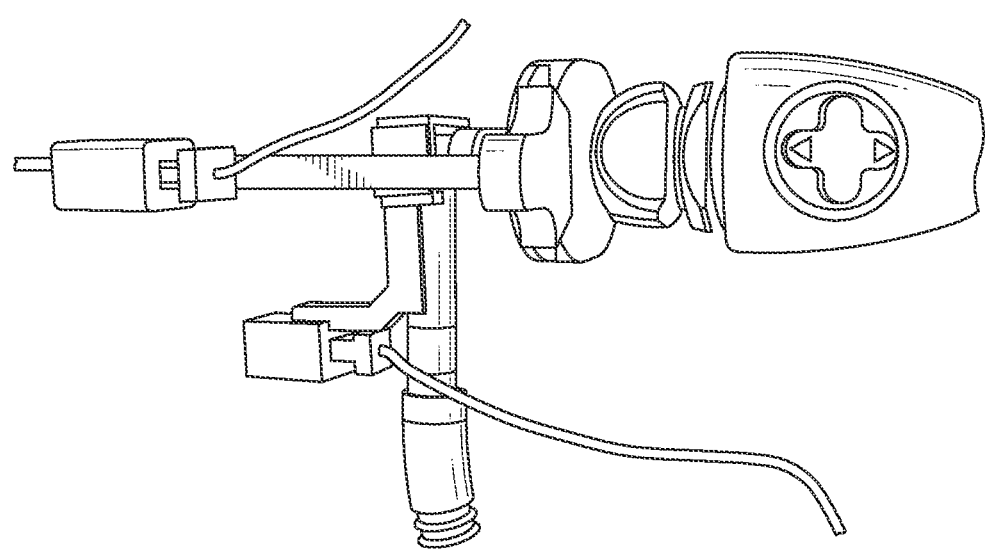
FIG. 5A is an illustration of an orientation of a laparoscope, according to an exemplary embodiment of the present disclosure.

It should be appreciated that the principal point may also rotate about $O_{IMG}$ while rotating the camera head relative to the telescope. Subsequently, let C(0) be the principal point calibrated at an initial state. A generic estimation of $O_{IMG}$ would be the midpoint of a line segment connecting C(0°) and C(180°) or, for instance, $$O_{IMG} = \frac{C(0°) + C(180°)}{2} \quad (2)$$

where C(180°) is the principal point estimated after a relative rotation of 180° from the initial state, shown in FIG. 5A. According to an embodiment, with the use of an algorithm implemented using software and/or hardware, such as fCalib, described above, calibration can be achieved rapidly. Based on the above estimation of $O_{IMG}$, the calibration, according to an embodiment of the present disclosure, may be performed as follows:

1) Obtain the rotation center in $EMS_1$'s (EM sensor on the telescope) coordinate system, $O_{EMS_1}$.

To this end, EM sensor spatial-tracking data may be recorded, via memory of or associated with a processing circuitry, at a frequency of 12 Hz for 15 seconds while the camera head is rotated relative to the telescope. After applying (1), this may yield a total of 180 sample points located on a circle centered at $O_{EMS_1}$. In an embodiment, $O_{EMS_1}$ may be calculated using the RANSAC algorithm with 2000 loops, for instance. The net calculation time for calculating $O_{EMS_1}$ may be less than 0.5 seconds.

2) Obtain a first, or initial, calibration using fCalib and record the current poses of each of two EM sensors (Pose 1).

According to an embodiment, calibration results may include camera intrinsic parameters, distortion coefficient, and extrinsic parameters. In an embodiment, the extrinsic parameters may be the results of a hand-eye calibration. Root-mean-square (RMS) re-projection error associated with the calibration results may be recorded in memory of or associated with a processing circuitry. In an example, the average time of calibration using fCalib may be 14 seconds.

3) Rotate the oblique-viewing rigid endoscope 180° from Pose 1.

FIG. 5A and FIG. 5B are illustrations of Pose 1 and Pose 2, respectively, of a laparoscope, according to an exemplary embodiment of the present disclosure. In an embodiment, and given $O_{EMS_1}$ obtained in Step (1) and Pose 1 obtained in Step (2), a relative rotation angle, θ, from Pose 1 may be calculated. As it may not be possible to manually rotate 180°, precisely, from Pose 1, θ∈[175°, 185°] may be selected, a range which can often be achieved through minimal adjustment of an initial rotation. As described, FIG. 5B is an illustration of a relative rotation, between a telescope and a camera head of an endoscope, of approximately 180°.

4) Obtain a second, or subsequent, calibration using fCalib, record Pose 2, and calculate $O_{IMG}$ according to (2).

According to an embodiment, the above-described step may complete a calibration. A comparison may be made between the two recorded calibrations and the calibration that minimizes RMS re-projection error may be set as the initial calibration, wherein its corresponding pose may be set as the initial pose.

According to an embodiment, after the calibration, a rotation angle, θ, can be calculated based on $O_{EMS_1}$ and the initial pose. The camera matrix can then be updated based upon θ, $O_{IMG}$, and the initial calibration.

In an embodiment, the calibration method may be implemented via C++ on a computer with 4-core 2.9 GHz Intel CPU and 8 GB of memory. OpenCV (Intel Corp., Santa Clara, Calif., USA) functions and Perceive 3D's SIC software may be incorporated into the calibration software. It should be appreciated that extrinsic parameters and distortion coefficient should not change with rotation.

Incidentally, it should be appreciated that it may be possible to calculate an exact $O_{IMG}$ based on two principal points and a rotation angle without implementing (2). Solving this problem mathematically, however, yields two possible solutions. While the distance to the image center may be used as a criterion from which to select one of the two solutions, this parameter, including the principal point, the image center, and $O_{IMG}$ may vary from oblique-viewing rigid endoscope to oblique-viewing rigid endoscope.

Updating Camera Matrix

According to an embodiment, the present disclosure further relates to updating the camera matrix with respect to clockwise (CW) (i.e., generating a clockwise rotation in the image) and/or counterclockwise (CCW) (i.e., generating a counterclockwise rotation in the image) rotations.

In an embodiment, let $(x_d, y_d)$ be the normalized pinhole projection after lens distortion, and $(x_p, y_p)$ be its corresponding pixel coordinates in an image. Thus, $$\begin{bmatrix} x_p \\ y_p \\ 1 \end{bmatrix} = K \begin{bmatrix} x_d \\ y_d \\ 1 \end{bmatrix} \quad (3)$$

where K is the camera matrix and may be simplified as $$K = \begin{bmatrix} f_x & 0 & C_x \\ 0 & f_y & C_y \\ 0 & 0 & 1 \end{bmatrix} \quad (4)$$

where $f_x$ and $f_y$ are focal lengths and C is a principal point. In an exemplary embodiment, the camera may be assumed to be skewless. Therefore, $O_{IMG}=(O_x, O_y)$ may be the rotation center in the image and $R_θ^+$ may be a CCW rotation matrix, wherein the CCW rotation may be defined as positive. A corrected projection, after CCW rotation of θ about $O_{IMG}$, may be expressed as $$\begin{bmatrix} x_c \\ y_c \\ 1 \end{bmatrix} = R_θ^+ \begin{bmatrix} x_p - O_x \\ y_p - O_y \\ 1 \end{bmatrix} + \begin{bmatrix} O_x \\ O_y \\ 1 \end{bmatrix} = \begin{bmatrix} \cos θ & -\sin θ & 0 \\ \sin θ & \cos θ & 0 \\ 0 & 0 & 0 \end{bmatrix} \begin{bmatrix} f_x x_d + C_x - O_x \\ f_y y_d + C_y - O_y \\ 1 \end{bmatrix} + \begin{bmatrix} O_x \\ O_y \\ 1 \end{bmatrix}$$

$$= \begin{bmatrix} \cos θ & -\sin θ & (1-\cos θ)O_x + \sin θ \cdot O_y \\ \sin θ & \cos θ & -\sin θ \cdot O_x + (1-\cos θ)O_y \\ 0 & 0 & 1 \end{bmatrix} \begin{bmatrix} f_x & 0 & C_x \\ 0 & f_y & C_y \\ 0 & 0 & 1 \end{bmatrix} \begin{bmatrix} x_d \\ y_d \\ 1 \end{bmatrix} + R_{θ, O_{IMG}^+} K \begin{bmatrix} x_d \\ y_d \\ 1 \end{bmatrix}$$

Similarly, the rotation matrix for the CW rotation can be expressed as $$R_{\theta,\overline{O}_{IMG}} \begin{bmatrix} \cos\theta & \sin\theta & (1-\cos\theta)O_x + \sin\theta \cdot O_y \\ -\sin\theta & \cos\theta & \sin\theta \cdot O_x + (1-\cos\theta)O_y \\ 0 & 0 & 1 \end{bmatrix} \quad (5)$$

For implementation, the above formulas may be used directly for correcting rotational offset. In an embodiment, implementation of the above-described formulas may result in multiplication by $R_{\theta,O_{IMG}}^{+}$ or $R_{\theta,O_{IMG}}^{-}$ on the left of the initial camera matrix.

Next, $p_{EMS_2}$ may be defined as an arbitrary point in $EMS_2$'s (EM sensor on the camera head) coordinate system while $p_{EMS_1}^{initial}$ may be its corresponding coordinates in $EMS_1$'s coordinate system, at the initial pose. Following subsequent rotation, the corresponding coordinates of $p_{EMS_2}$ in $EMS_1$'s coordinate system may change to $p_{EMS_1}$. The direction of rotation, therefore, CW or CCW, may be determined according to $$\text{sgn}([(O_{EMS_1} - p_{EMS_1}^{initial}) \times (O_{EMS_1} - p_{EMS_2})]_z) \quad (6)$$

where $O_{EMS_1}$ may be the obtained rotation center in $EMS_1$'s coordinate system.

According to an embodiment of the present disclosure, the above-described calibration method may be performed in whole or in part using a processing circuitry of an oblique-viewing rigid endoscope.

According to an embodiment, in the event that the error is determined to be unacceptable, for instance, after a significant rotation, re-calibration via fCalib, in order to reset the initial calibration and the initial pose, may remain an option. In an example, for ultrasound-based augmented reality applications, a top edge of an overlaid ultrasound image may be expected to align with a bottom edge of imaging elements of a laparoscopic ultrasound transducer. However, if there is incongruence between these elements following, for instance, a large rotation, re-initialization of the calibration may be performed.

Non-Limiting Experimental Information

Experiment 1

According to an embodiment of the present disclosure, methods to obtain a rotation center in an image $O_{IGM}$ may be evaluated. Following attachment of one or more EM sensor mounts, five freehand calibrations may be performed according to the above-described calibration steps (Steps 1-4). In an embodiment, a starting relative angle between a telescope and a camera head of a laparoscope may be gradually increased approximately 30°-40° between two consecutive calibration trials. During image acquisition, the distance between the laparoscopic lens at a distal end of telescope and the center of the fCalib plate may be a typical clinical operating distance of a laparoscope. In an example, the distance between the laparoscopic lens at the distal end to the telescope and the center of the fCalib plate may range from 7 centimeters to 9 centimeters.

Experiment 2

As described above, during Step 3 of the calibration method, a rotation of 180°±5° from Pose 1 may be made in order to yield Pose 2. According to an embodiment, additional calibration trials, wherein the angle of rotation between Pose 1 and Pose 2 are approximately 170°, 160° and 150°, may be performed.

Experiment 3

Figure 6:
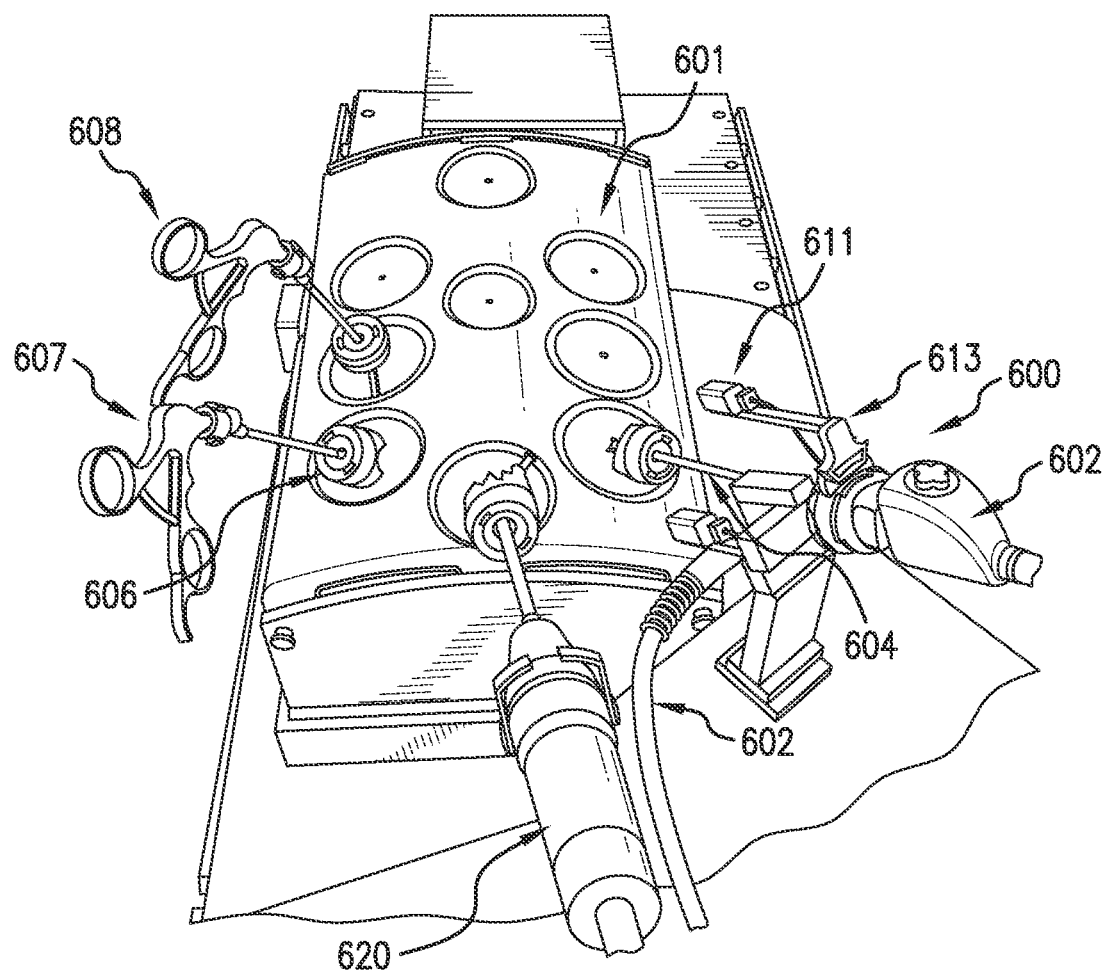
FIG. 6 is an illustration of a simulated clinical environment, according to an exemplary embodiment of the present disclosure.

According to an embodiment, the static calibration accuracy of the above-described calibration method may be validated. To this end, experiments were performed in a simulated clinical environment, as shown in FIG. 6, in order to reduce errors in EM sensor spatial-tracking resulting from the presence of metallic and/or conductive materials. In an embodiment, a tabletop field generator may be placed on a surgical table near the simulated clinical environment. A laparoscopic trainer 601 simulating a patient's abdomen may be placed on the field generator. In an embodiment, the laparoscopic trainer 601 may be a plastic laparoscopic trainer. One or more laparoscopic surgical tools, including one grasper 607 and one pairs of scissors 608, may be inserted into the laparoscopic trainer 601 through a corresponding one or more trocars 606. In an embodiment, and in order to simulate the use of a laparoscope in an ultrasound-based augmented reality system, a laparoscopic ultrasound probe 620 may be inserted into the laparoscopic trainer 601. Further, the laparoscopic ultrasound probe 620 may be connected to an ultrasound scanner, the ultrasound scanner remaining active during experimentation.

According to an embodiment, the fCalib plate may then be placed inside the laparoscopic trainer 601. In an embodiment, the fCalib plate may be used only for corner point detection. A laparoscope 600, comprising a camera head 602, a telescope 604, a light source, and one or more EM sensors 611 within one or more EM sensor mounts 613 may be inserted into the laparoscopic trainer 601 through a 5-mm trocar 606. The laparoscope 600 may be supported such that hand tremor may be eliminated.

According to an embodiment, calibration results ($O_{EMS_1}$, $O_{IMG}$, initial calibration, initial pose) from one of the five freehand calibration trials of Experiment 1 may be selected and implemented. The camera head 602 may be rotated relative to the telescope 604, in incremented angles, both CW and CCW. Following each rotation, an image of a calibration pattern of a calibration plate may be acquired and corner points may be automatically detected in the image. A rotation angle $\theta$ may be calculated from $O_{EMS_1}$, the initial pose, and the current pose based upon spatial-tracking data of the two EM sensors 611. A rotation-corrected projection of corner points ($p_{cor}$) may be obtained from $O_{IMG}$, $\theta$, and the initial calibration and may be compared with detected corner points ($p_{det}$) using the RMS re-projection error, defined as $$\text{error} = \sqrt{\frac{1}{N} \sum_{i=1}^{N} d(p_{cor}^i, p_{det}^i)^2} \quad (7)$$

where N is a number of detected corner points and $d(\cdot,\cdot)$ is a Euclidean distance in pixels. It can be appreciated that the SIC method of the present disclosure may be employed to detect as many corner points as possible in any visible part of the calibration pattern.

Experiment 4

According to an embodiment, and in order to further evaluate dynamic calibration accuracy for practical use, a virtual tube overlay may be visually examined using a calibration plate of the fCalib method. Notably, a feature of the fCalib method is the ability to immediately evaluate calibration accuracy by overlaying a virtual tube model on a camera image. In an embodiment, this feature may be used in order to overlay the rotation-corrected virtual tube on the image. In an example, visual agreement between the virtual tube model and the actual tubes in the image may indicate accurate calibration and rotation correction.

According to an embodiment, calibration of an oblique-viewing rigid laparoscope may be performed following the above-described procedure. The oblique-viewing rigid laparoscope may then be inserted into a laparoscopic trainer, wherein the laparoscopic trainer comprises one or more ancillary surgical tools. A calibration plate of the fCalib method may also be placed inside the laparoscopic trainer such that a tube phantom coupled to the calibration plate may simulate a target structure. In an embodiment, the target structure may include but is not limited to a blood vessel or bile duct. The two parts of the oblique-viewing rigid laparoscope may then be rotated at discretionary angles in the CW and CCW directions. During each rotation, a telescope of the oblique-viewing rigid endoscope may be held stable while a camera head of the oblique-viewing rigid endoscope may be rotated in order to maintain the tube phantom of the calibration plate in the field of view. The resulting virtual tube model, generated before and after rotation correction, may be visualized via video. In an embodiment, and in order to trigger rotation correction, a button may be pressed using a foot pedal. It should be appreciated than any method of triggering rotation correction, including but not limited to voice-operated and touch-operated methods, may be appropriate and implemented. Following rotation correction, the oblique-viewing rigid laparoscope may be moved, at the discretion of a user, in order to visually assess the accuracy of the overlay between the actual tube and virtual tube model.

Results—Experiment 1

In an embodiment, the time required to complete one calibration ranged from 1 minute and 50 seconds to 2 minutes and 25 seconds. In an example, the time required to complete one calibration required an average of 2 minutes and 8 seconds. Table 1, shown below, describes the results from Step 1 of the five calibration trials. Further, Table 1 indicates that corresponding estimated $O_{EMS_1}$ is consistent across each of the five calibration trials.

TABLE 1

Results from Step 1 of the five freehand calibrations

| | $O_{EMS_1}{}^a$ (mm) | Distance $^b$ (mm) |
|---|---|---|
| Calibration 1 | (−32.6, −38.6, −7.8) | 54.2 ± 0.6 |
| Calibration 2 | (−32.9, −38.5, −8.5) | 53.2 ± 0.7 |
| Calibration 3 | (−32.1, −38.4, −8.0) | 54.6 ± 0.6 |
| Calibration 4 | (−32.8, −38.4, −8.3) | 53.9 ± 0.7 |
| Calibration 5 | (−33, −38.2, −9.0) | 53.9 ± 0.7 |

Figure 7:
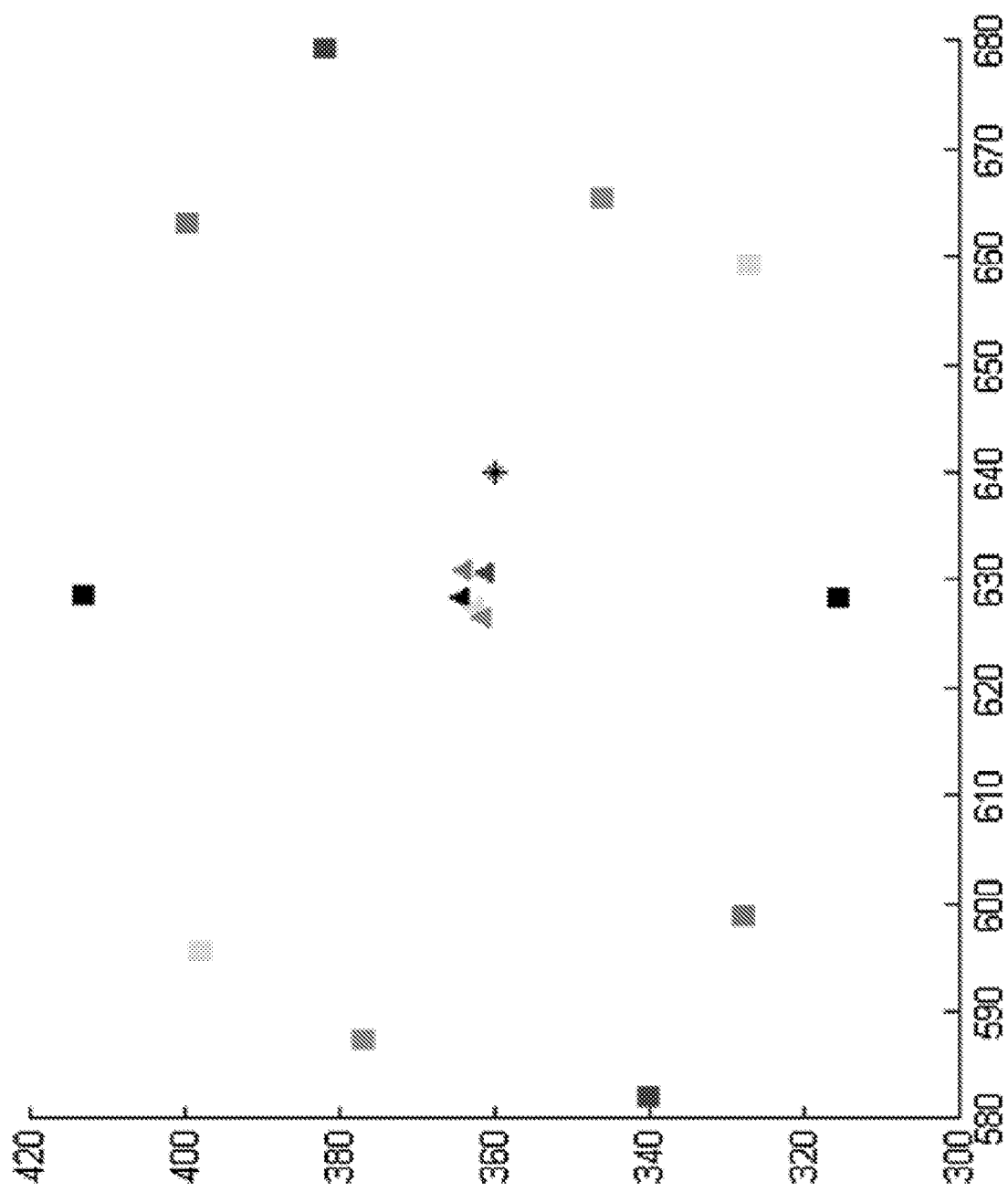
FIG. 7 is a graphical illustration of a comparison of a rotation center of an image, estimated principal points, and an image center, according to an exemplary embodiment of the present disclosure.

$^a$ 3-D rotation center in EMS$_1$'s (EM sensor on the telescope) coordinate system
$^b$ Distance from $O_{EMS_1}$ to the collected sample points located on the circle centered at $O_{EMS_1}$ FIG. 7 is a graphical illustration of a comparison of a rotation center of an image, estimated principal points, and an image center, according to an exemplary embodiment of the present disclosure. Specifically, FIG. 7 provides a comparison of the rotation center in the image $O_{IMG}$ (triangle), the principal points (square), and the image center (star), wherein each $O_{IMG}$ may be calculated using two principal points of the same color. Further, the image resolution may be 1280×720 pixels.

In particular, according to an embodiment, FIG. 7 illustrates the estimated principal points (two in each calibration), the calculated $O_{IMG}$, and the image center. In an example, the image center may be (640, 360). Actual rotation angles between a first calibration and a second calibration ranged from 176.5° to 179.7°. In an example, the ideal rotation angle between the first calibration and the second calibration may be 180°. As shown in FIG. 7, the calculated $O_{IMG}$ was stable, differing considerably from the respective principal points and differing only slightly from the image center. In an embodiment, excepting the varying principal points, other calibrated parameters, including the focal length and the distortion coefficient, were consistent among different calibration trials. In an exemplary embodiment, the 10 SICs (two in each calibration) yielded 1.2±0.2 pixel RMS re-projection error.

Results—Experiment 2

According to an embodiment, and based on the results from Experiment 1, it may be reasonable to assume a ground truth $O_{IMG}{}^{ref}$ to be an average of the five above-calculated $O_{IMG}$. In an embodiment, θ may be a rotation angle between Pose 1 and Pose 2. Table 2 describes several distances from $O_{IMG}{}^{ref}$, including (1) $O_{IMG}{}^{ref}$ to $O_{IMG}$ of the five calibrations in Experiment 1, (2) $O_{IMG}{}^{ref}$ the image center, and (3) $O_{IMG}{}^{ref}$ to $O_{IMG}$ of the three additional calibration trials in Experiment 2. In an example, results suggest that a rotation of 180°±5° between Pose 1 and Pose 2 may be beneficial or necessary.

TABLE 2

Distance from $O_{IMG}{}^{ref}$ to $O_{IMG}$ (with various θ) and image center

| | θ ∈ [175°, 185°] | θ ≈ 170° | Image center | θ ≈ 160° | θ ≈ 150° |
|---|---|---|---|---|---|
| Distance (pixel) | [1.4, 2.6] | 7.7 | 11.3 | 12.4 | 16.1 |

Results—Experiment 3

Figure 8:
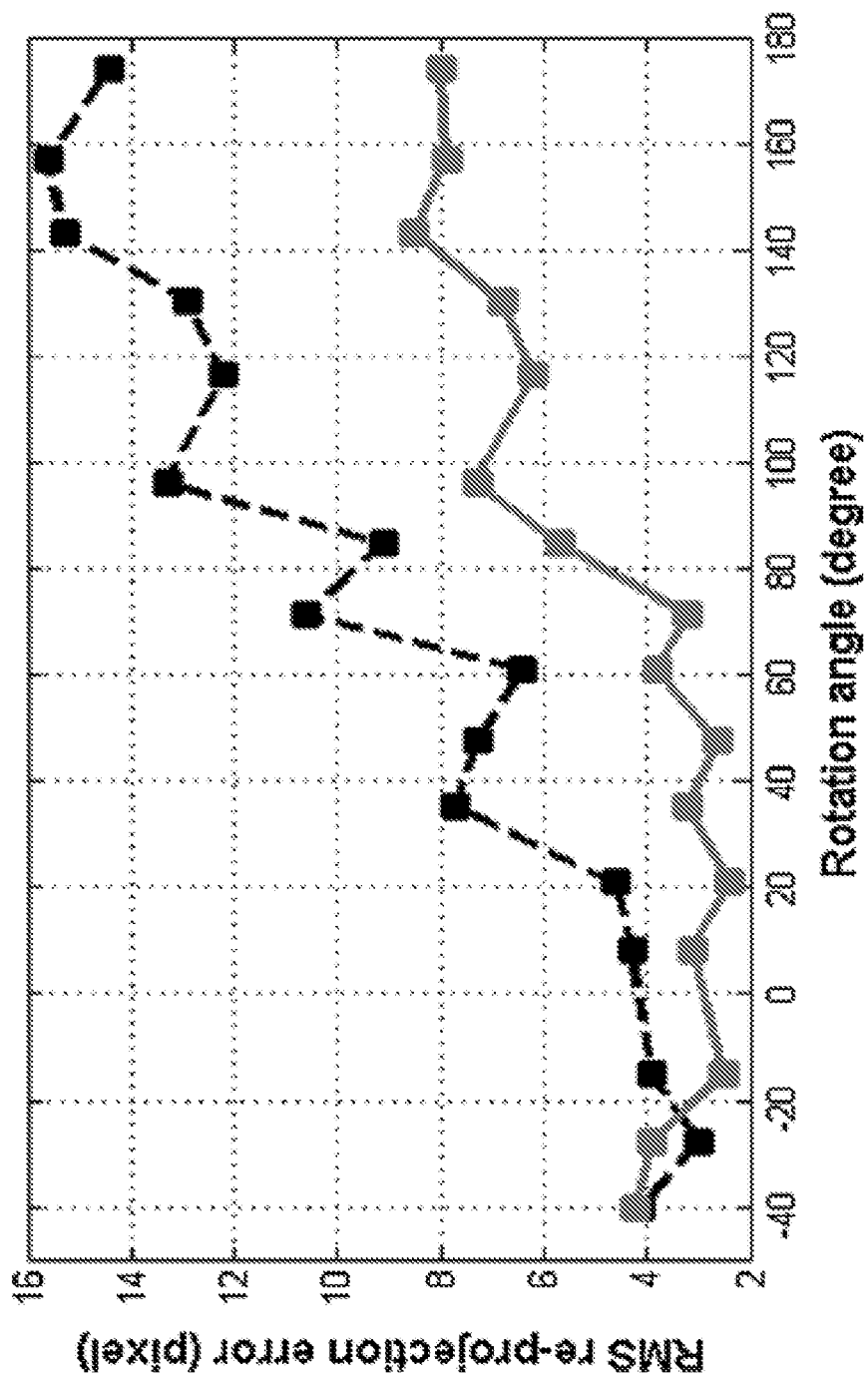
FIG. 8 is a graphical illustration of a RMS re-projection error comparing a rotation-corrected projection of corner points and the detected corner points, according to an exemplary embodiment of the present disclosure.

FIG. 8 is a graphical illustration of a RMS re-projection error comparing a rotation-corrected projection of corner points and the detected corner points, according to an exemplary embodiment of the present disclosure. Specifically, FIG. 8 demonstrates an RMS re-projection error using the method of the present disclosure. In an example, the RMS re-projection error using the method of the present disclosure may range from 2.5 pixels to 8.5 pixels. As reference, FIG. 8 illustrates the RMS re-projection error of an approach using image center as the rotation center in an image. Combined with Table 2, it may be observed that an increasing distance from $O_{IMG}{}^{ref}$ yields an inferior RMS re-projection error.

Figure 9:
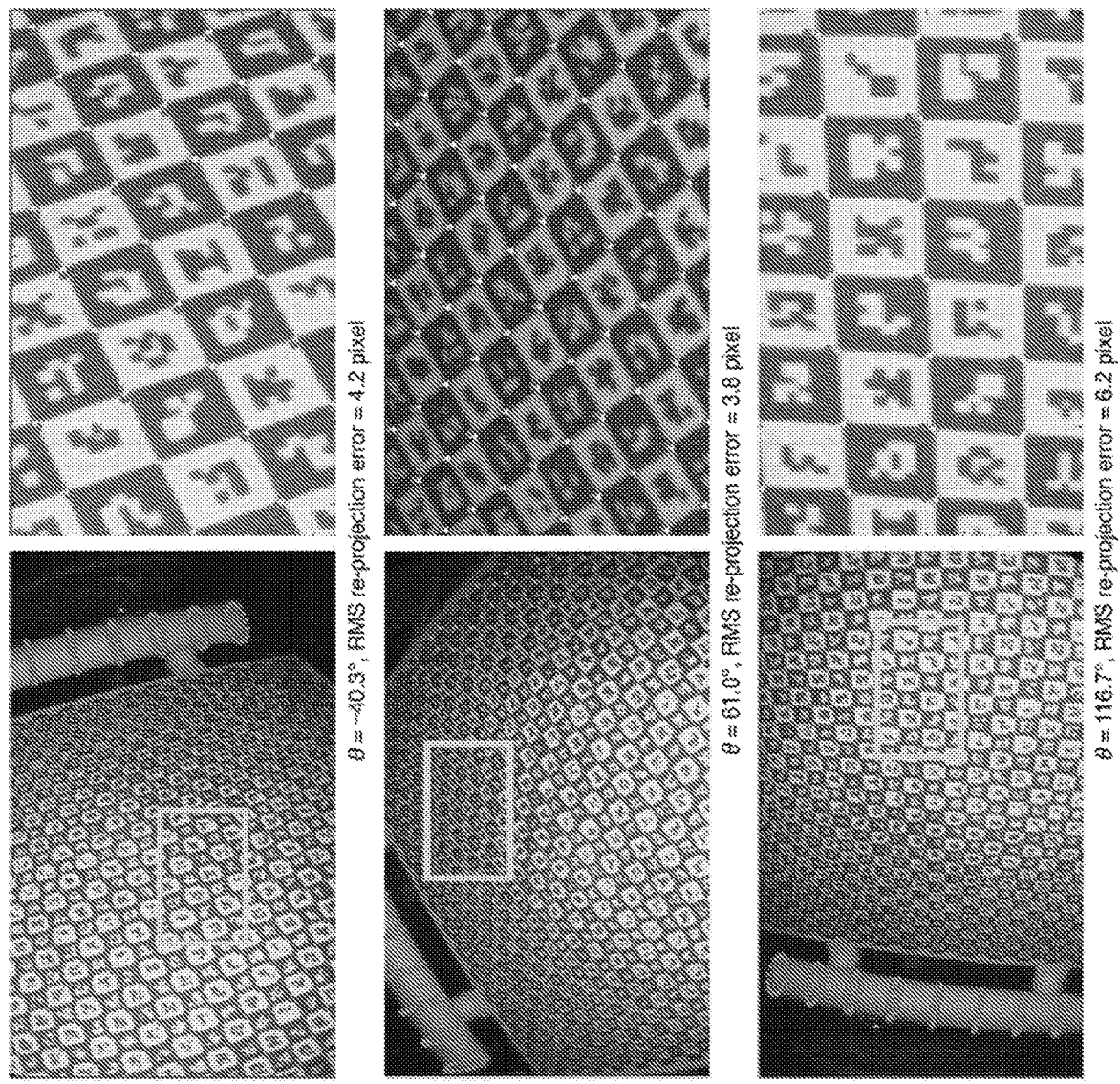
FIG. 9 is an illustration of a rotation-corrected projection of corner points superimposed on an original image, according to an exemplary embodiment of the present disclosure.

According to an embodiment, and as a qualitative evaluation of the static accuracy of the method of the present disclosure, rotation-corrected projections of corner points may be superimposed on corresponding original images at three different rotation angles. FIG. 9 is an illustration of a rotation-corrected projection of corner points superimposed on an original image, according to an exemplary embodiment of the present disclosure. Specifically, the magnified views of FIG. 9 demonstrate the correlation between the detected corner points and the rotation-corrected projection of corresponding corner points.

In an embodiment, FIG. 9 demonstrates, at a macroscopic level, the rotation-corrected projection of corner points superimposed on the original image. Further, the image may also demonstrate an overlay of the rotation-corrected virtual tube (a series of rings) and the actual tube. In another embodiment, FIG. 9 demonstrates, at a microscopic level, a magnified view illustrating the rotation-corrected projection of corner points (circles) and the detected corner points (triangles).

Results—Experiment 4

Figure 10C:
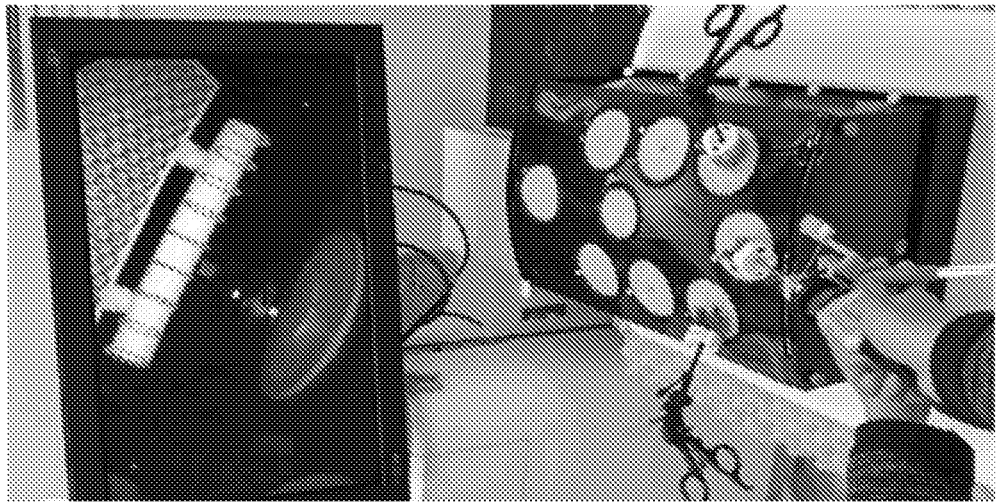
FIG. 10C is an illustration of an aspect of a use of a laparoscope, according to an exemplary embodiment of the present disclosure.
Figure 10B:
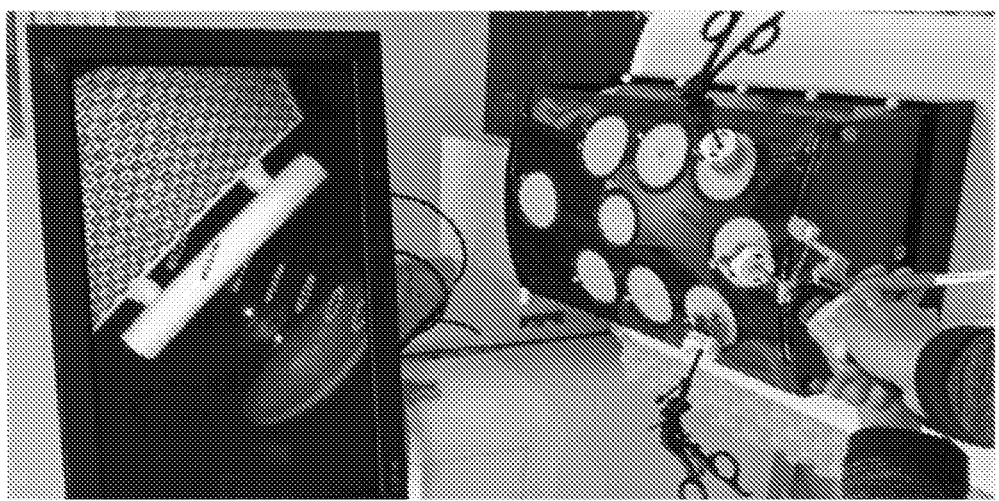
FIG. 10B is an illustration of an aspect of a use of a laparoscope, according to an exemplary embodiment of the present disclosure.
Figure 10A:
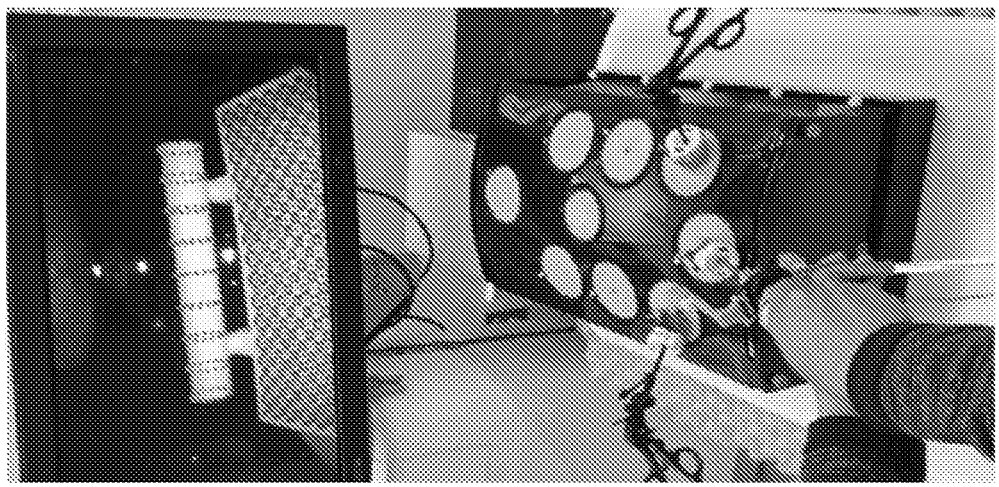
FIG. 10A is an illustration of an aspect of a use of a laparoscope, according to an exemplary embodiment of the present disclosure.

According to an embodiment, three snapshots from a video clip demonstrating handling of a laparoscope, as well as an overlay of the virtual tube and the actual tube, are shown in FIG. 10A, FIG. 10B, and FIG. 10C.

FIG. 10A, FIG. 10B, and FIG. 10C are illustrations of an aspect of a use of a laparoscope, according to an exemplary embodiment of the present disclosure. Generally, the snapshots from the video clip represent handling of the laparoscope and the overlay of the virtual tube and the actual tube. Specifically, FIG. 10A is an illustration of the laparoscope in an initial state, prior to rotation. It can be appreciated that the virtual tube and the actual tube are in agreement. FIG. 10B is an illustration of the laparoscope after rotation but before rotation correction in the image may be applied. It can be appreciated that the virtual tube and the actual tube are not in agreement. FIG. 10C is an illustration of the laparoscope after rotation and following application of rotation correction. It can be appreciated that the virtual tube and the actual tube are, again, in agreement.

With regard to FIG. 10, in addition to rotation-related errors, error resulting from EM sensor tracking and the initial calibration may also occur. As shown in FIG. 10, overlay error begins to change direction, relative to a center line of the actual tube, when the actual tube crosses the center of the camera image. In an embodiment, this may be an effect imparted by dynamic EM sensor tracking error and an error in radial distortion estimation. In an example, the error in radial distortion estimation may cause extra inward or outward displacement of a point from a corresponding ideal location. It should be noted that this phenomenon also occurs for forward-viewing rigid endoscopes. Generally, however, spatial agreement was found between the rotation-corrected virtual tube and the actual tube, wherein the rotation-correction was determined and implemented in real time.

Accordingly, the calibration method according to an embodiment of the present disclosure may be validated using a conventional 30°, 5-mm oblique-viewing rigid laparoscope. Freehand calibrations may be performed using the method of the present disclosure. In an example, average calibration time was 2 minutes and 8 seconds. Further, calibration accuracy may be evaluated in a simulated clinical setting including a variety of ancillary surgical tools, wherein the variety of ancillary surgical tools are positioned within a magnetic field of a tabletop field generator configured for use in EM sensor tracking. In an embodiment, RMS re-projection error ranged from 2.4 pixels to 8.5 pixels with an image resolution of 1280×720 for rotation angles between −40.3° and 174.7°. In an example, RMS re-projection error averaged 4.9 pixels.

Figure 11:
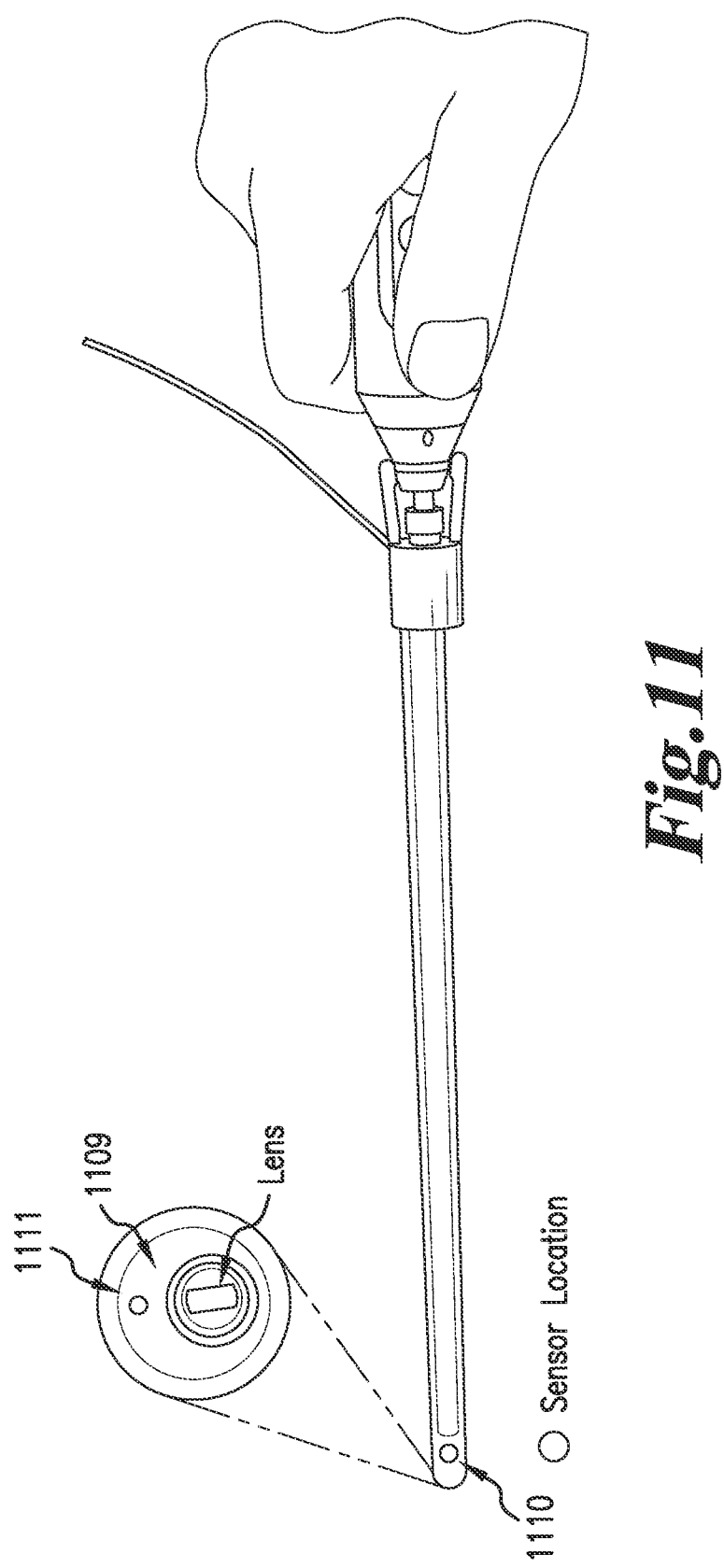
FIG. 11 is an illustration of an aspect of an endoscope, according to an exemplary embodiment of the present disclosure.

FIG. 11 is an illustration of an aspect of an endoscope, according to an exemplary embodiment of the present disclosure. In an embodiment, an endoscope comprises a protective sheath, the protective sheath enclosing a circumferential surface of the endoscope. At a distal end of the endoscope, a lens 1109 is exposed for image acquisition. Further, a spatial-tracking sensor 1110 is disposed within the distal end of the endoscope. In an example, the spatial-tracking sensor 1110 may be an EM sensor 1111.

Figure 12:
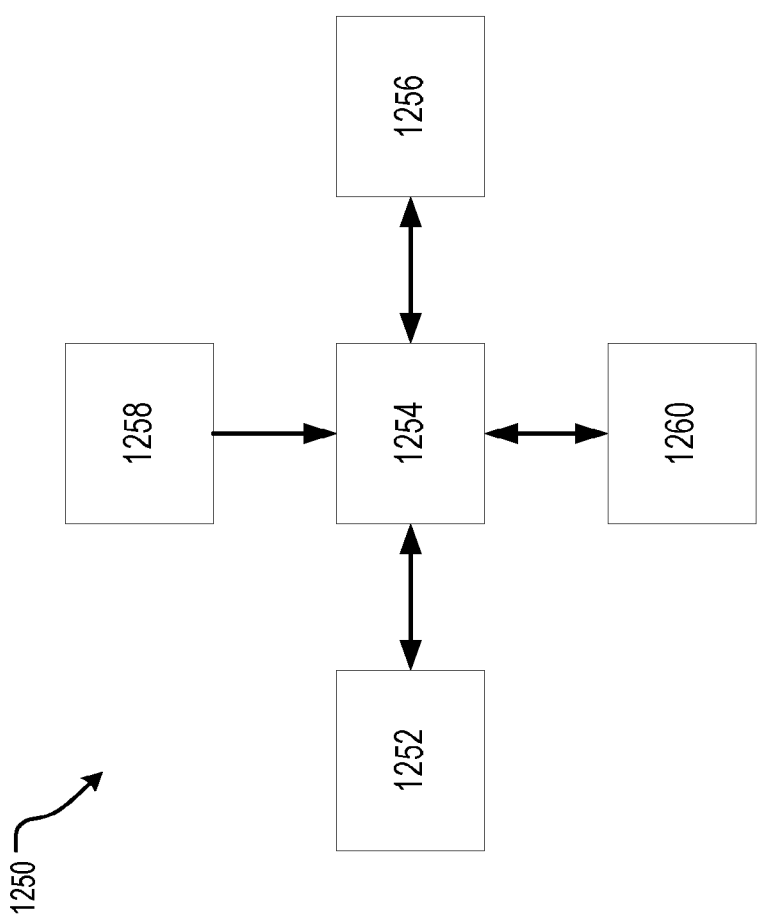
FIG. 12 is a block diagram of a system or an apparatus, according to an exemplary embodiment of the present disclosure.

FIG. 12 is a block diagram of a system or an apparatus, according to an exemplary embodiment of the present disclosure. Specifically, the block diagram is of a system or an apparatus 1250, referred to herein as "system 1250'.

Generally, system 2150 may be comprised of an oblique-viewing rigid endoscope (not expressly shown) having, inter alia, a camera 1252, a processing circuitry 1254, a memory device 1256, a spatial-tracking subsystem 1258, and a display device 1260. The camera 1252, the memory device 1256, the spatial-tracking subsystem 1258, and the display device 1260 may be operatively coupled to the processing circuitry 1254.

Generally, the spatial-tracking subsystem 1258 may include one or more spatial-tracking sensors, a first spatial-tracking sensor coupled to a camera head of the oblique-viewing rigid endoscope and a second spatial-tracking sensor coupled to a telescope of the oblique-viewing rigid endoscope. The spatial-tracking subsystem 1258 may be configured to track relative rotation between the telescope and the camera head. In an embodiment, the spatial-tracking subsystem 1258 may be comprised of one or more EM sensors. In an example, the one or more EM sensors may be selected from a group including but not limited to conducting spheres, loop conductors, inductors, and antennas. In another embodiment, the spatial-tracking subsystem 1258 may be comprised of a combination of one or more EM sensors and one or more rotary encoders. In an example, the one or more rotary encoders may be selected from the group including but not limited to an absolute encoder and an incremental encoder. Further, the one or more rotary encoders may include but are not limited to mechanical absolute encoders, optical absolute encoders, magnetic absolute encoders, capacitive absolute encoders, battery-powered multi-turn encoders, geared multi-turn encoders, and self-powered multi-turn encoders. In another embodiment, one of the one or more spatial-tracking sensors of the spatial-tracking subsystem 1258 may be fabricated integrally with a component of the oblique-viewing rigid endoscope.

According to an embodiment, the processing circuitry 1254 may be configured to perform a single-image calibration operation in order to compensate for a rotational offset between an actual object and a projection of an object in an image of the camera 1252, wherein the offset may be due to the relative rotation between the telescope and the camera head as tracked by the spatial-tracking subsystem 1258. Further, the processing circuitry 1254 may be embodied as various means for implementing the various functionalities of exemplary embodiments of the present disclosure including but not limited to a microprocessor, a coprocessor, a controller, a special-purpose integrated circuit such as, for example, an application specific integrated circuit (ASIC), a field programmable gate array (FPGA), a hardware accelerator, a processing circuitry and/or the like. According to one or more embodiments of the present disclosure, the processing circuitry 1254 may be representative of a plurality of processors, or one or more multiple core processors, operating in concert. Further, the processing circuitry 1254 may be comprised of a plurality of transistors, logic gates, a clock, e.g., oscillator, other circuits or circuitry, and/or the like to facilitate performance of the functionality described herein. The processing circuitry 1254 may, but need not, include one or more accompanying digital signal processors. In an exemplary embodiment, the processing circuitry 1254 may be configured to execute instructions stored in the memory device 1256 or instructions otherwise accessible to the processing circuitry 1254. The processing circuitry 1254 may be further configured to operate such that the processing circuitry 1254 causes the apparatus to perform various functionalities described herein.

According to an embodiment, whether configured as hardware or via instructions stored on a computer-readable storage medium, or by a combination thereof, the processing circuitry 1254 may be an entity configured to perform, and/or cause the system 1250 to perform, operations according to exemplary embodiments of the present disclosure while configured accordingly, including some or all of the Steps (1)-(4) discussed above. Thus, in exemplary embodiments where the processing circuitry 1254 is embodied as, or is part of, an ASIC, FPGA, or the like, the processor may be specifically configured hardware for conducting, or causing the performance of, the operations described herein. Alternatively, in exemplary embodiments where the processing circuitry 1254 is embodied as an executor of instructions stored on a computer-readable storage medium, the instructions can specifically configure the processing circuitry 1254 to perform, and/or cause the performance of, the algorithms and operations described herein. In some exemplary embodiments, the processing circuitry 1254 can be a processing circuitry of a specific device configured for employing exemplary embodiments of the present disclosure by further configuration of the processing circuitry 1254 via executed instructions for performing, and/or causing the performance of, the algorithms, methods, and operations described herein.

The memory device 1256 may be one or more computer-readable storage media that may include volatile and/or non-volatile memory. In some example embodiments, the memory device 1256 can include Random Access Memory (RAM) including dynamic and/or static RAM, on-chip or off-chip cache memory, and/or the like. Further, the memory device 1256 may include non-volatile memory, which may be embedded and/or removable, and may include, for example, read-only memory, flash memory, magnetic storage devices, e.g., hard disks, magnetic tape, etc., optical disc drives and/or media, non-volatile random access memory (NVRAM), and/or the like. The memory device 1256 may include a cache area for temporary storage of data. In this regard, at least a portion or the entire memory device 1256 may be included within the processor 1254.

Further, according to an embodiment, the memory device 1256 may be configured to store information, data, applications, computer-readable program code instructions, and/or the like for enabling the processing circuitry 1254 and the example apparatus or system to carry out various functions in accordance with exemplary embodiments of the present disclosure described herein. In an example, the memory device 1256 may be configured to buffer input data for processing by the processing circuitry 1254. Additionally, or alternatively, the memory device 1256 may be configured to store instructions for execution by the processing circuitry 1254.

Figure 13:
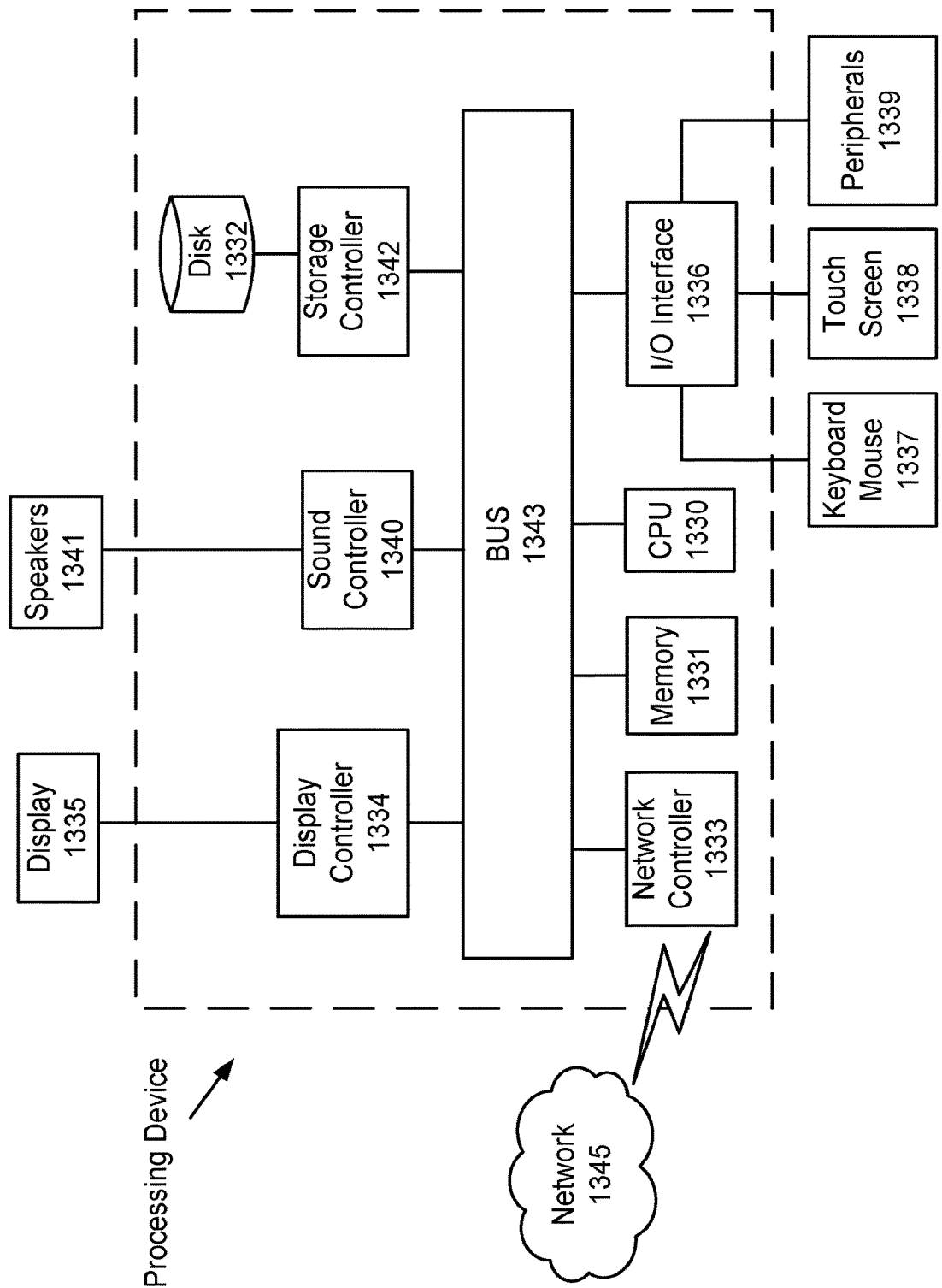
FIG. 13 is a hardware description of a processing device of a system or an apparatus, according to an exemplary embodiment of the present disclosure.

According to an embodiment, the method of the present disclosure may be executed via a processing device. In another embodiment, the processing device may be a laptop, personal computer, server, or mobile device. FIG. 13 is a hardware description of a processing device of a system or an apparatus, according to an exemplary embodiment of the present disclosure.

In FIG. 13, the processing device includes a CPU 1343 which performs the processes described above. The process data and instructions may be stored in memory 1331. These processes and instructions may also be stored on a storage medium disk 1332 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RANI, ROM, PROM, EPROM, EEPROM, hard disk or any other information processing device with which the processing device communicates, such as a server or computer.

Further, the claimed advancements may be provided as a utility application, background daemon, or component of an operating system, or combination thereof, executing in conjunction with CPU 1330 and an operating system such as Microsoft Windows 7, UNIX, Solaris, LINUX, Apple MAC-OS and other systems known to those skilled in the art.

The hardware elements in order to achieve the processing device may be realized by various circuitry elements, known to those skilled in the art. For example, CPU 1330 may be a Xenon or Core processor from Intel of America or an Opteron processor from AMD of America, or may be other processor types that would be recognized by one of ordinary skill in the art. Alternatively, the CPU 1330 may be implemented on an FPGA, ASIC, PLD or using discrete logic circuits, as one of ordinary skill in the art would recognize. Further, CPU 1330 may be implemented as multiple processors cooperatively working in parallel to perform the instructions of the inventive processes described above.

The processing device in FIG. 13 also includes a network controller 1333, such as an Intel Ethernet PRO network interface card from Intel Corporation of America, for interfacing with network 1345. As can be appreciated, the network 1345 can be a public network, such as the Internet, or a private network such as an LAN or WAN network, or any combination thereof and can also include PSTN or ISDN sub-networks. The network 1345 can also be wired, such as an Ethernet network, or can be wireless such as a cellular network including EDGE, 3G and 4G wireless cellular systems. The wireless network can also be WiFi, Bluetooth, or any other wireless form of communication that is known.

The processing device further includes a display controller 1334, such as a NVIDIA GeForce GTX or Quadro graphics adaptor from NVIDIA Corporation of America for interfacing with display 1335, such as a Hewlett Packard HPL2445w LCD monitor. A general purpose I/O interface 1336 interfaces with a keyboard and/or mouse 1337 as well as a touch screen panel 1338 on or separate from display 1335. General purpose I/O interface also connects to a variety of peripherals 1339 including printers and scanners, such as an OfficeJet or DeskJet from Hewlett Packard.

A sound controller 1340 is also provided in the processing device, such as Sound Blaster X-Fi Titanium from Creative, to interface with speakers/microphone 1341 thereby providing sounds and/or music.

The general purpose storage controller 1342 connects the storage medium disk 1332 with communication bus 1343, which may be an ISA, EISA, VESA, PCI, or similar, for interconnecting all of the components of the processing device. A description of the general features and functionality of the display 1335, keyboard and/or mouse 1337, as well as the display controller 1334, storage controller 1342, network controller 1333, sound controller 1340, and general purpose I/O interface 1336 is omitted herein for brevity as these features are known.

Embodiments of the present disclosure may also be as set forth in the following parenthetical s.

(1) A system for performing a calibration operation, comprising a rigid endoscope, including a telescope, a camera head having a camera and being rotatably coupled to the telescope, one or more spatial-tracking sensors, and a processing circuitry configured to obtain a rotation center of a first one of the one or more spatial-tracking sensors, the first one of the one or more spatial-tracking sensors being disposed on the telescope of the rigid endoscope, the telescope of the rigid endoscope being in a first pose, obtain a first calibration, the first calibration being related to the first pose, rotate, to a second pose, the telescope of the rigid endoscope relative to the camera head of the rigid endoscope, obtain a second calibration, the second calibration being related to the second pose, and select from the first calibration and the second calibration based upon a comparison of an error value between the first calibration and the second calibration, wherein a second one of the one or more spatial-tracking sensors is disposed on the camera head, and wherein the rotation of the telescope of the rigid endoscope relative to the camera head of the rigid endoscope is based upon a relative position of the first one of the one or more spatial-tracking sensors and the second one of the one or more spatial-tracking sensors.

(2) The system according to (1), wherein each calibration of the calibration operation is a single-image calibration operation.

(3) The system according to either (1) or (2), wherein the calibration operation is an initial calibration operation.

(4) The system according to any of (1) to (3), wherein the calibration operation is an update to the initial calibration operation.

(5) The system according to any of (1) to (4), wherein at least one of the one or more spatial-tracking sensors is a rotary encoder.

(6) The system according to any of (1) to (5), wherein the processing circuitry is further configured to estimate a rotation center of an image based upon the first pose and the second pose, the first pose and the second pose corresponding to principal points of the image.

(7) The system according to any of (1) to (6), wherein the processing circuitry is further configured to update a camera matrix according to a direction of the rotation, the camera matrix being based upon a rotation angle, an image center, and the calibration operation.

(8) A method of performing a calibration operation, comprising obtaining, via processing circuitry, a rotation center of a first one of one or more spatial-tracking sensors, the first one of the one or more spatial-tracking sensors being disposed on a telescope of a rigid endoscope, the telescope of the rigid endoscope being in a first pose, obtaining, via the processing circuitry, a first calibration, the first calibration relating to the first pose, rotating, to a second pose, the telescope of the rigid endoscope relative to a camera head of the rigid endoscope, obtaining, via the processing circuitry, a second calibration, the second calibration relating to the second pose, and selecting, via the processing circuitry, from the first calibration and the second calibration based upon a comparison of an error value between the first calibration and the second calibration, wherein a second one of the one or more spatial-tracking sensors is disposed on the camera head of the rigid endoscope, and wherein the rotation of the telescope of the rigid endoscope relative to the camera head of the rigid endoscope is based upon a relative position of the first one of the one or more spatial-tracking sensors and the second one of the one or more spatial-tracking sensors.

(9) The method according to (8), wherein each calibration of the calibration operation is a single-image calibration operation.

(10) The method according to either (8) or (9), wherein the calibration operation is an initial calibration operation.

(11) The method according to any of (8) to (10), wherein the calibration operation is an update to the initial calibration operation.

(12) The method according to any of (8) to (11), wherein at least one of the one or more spatial-tracking sensors is a rotary encoder.

(13) The method according to any of (8) to (12), further comprising estimating, via the processing circuitry, a rotation center of an image based upon the first pose and the second pose, the first pose and the second pose corresponding to principal points of the image.

(14) The method according to any of (8) to (13), further comprising updating, via the processing circuitry, a camera matrix according to a direction of the rotation, the camera matrix being based upon a rotation angle, an image center, and the calibration operation.

(15) A non-transitory computer-readable storage medium storing computer-readable instructions that, when executed by a computer having a processing circuitry, cause the computer to perform a calibration operation, the calibration operation comprising obtaining a rotation center of a first one of one or more spatial-tracking sensors, the first one of the one or more spatial-tracking sensors being disposed on a telescope of a rigid endoscope, the telescope of the rigid endoscope being in a first pose obtaining a first calibration, the first calibration relating to the first pose, obtaining a second calibration, the second calibration relating to a second pose, and selecting from the first calibration and the second calibration based upon a comparison of an error value between the first calibration and the second calibration, wherein the second pose is achieved by rotating the telescope of the rigid endoscope relative to a camera head of the rigid endoscope, wherein a second one of the one or more spatial-tracking sensors is disposed on the camera head of the rigid endoscope, and wherein the rotation of the telescope of the rigid endoscope relative to the camera head of the rigid endoscope is based upon a relative position of the first one of the one or more spatial-tracking sensors and the second one of the one or more spatial-tracking sensors.

(16) The method according to (15), wherein each calibration of the calibration operation is a single-image calibration operation.

(17) The method according to either (15) or (16), wherein the calibration operation is an initial calibration operation.

(18) The method according to any of (15) to (17), wherein the calibration operation is an update to the initial calibration operation.

(19) The method according to any of (15) to (18), further comprising estimating a rotation center of an image based upon the first pose and the second pose, the first pose and the second pose corresponding to principal points of the image.

(20) The method according to any of (15) to (19), further comprising updating a camera matrix according to a direction of the rotation, the camera matrix being based upon a rotation angle, an image center, and the calibration operation.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A system for performing a calibration operation, comprising:
a rigid endoscope, including:
a telescope;
a camera head having a camera and being rotatably coupled to the telescope;
one or more spatial-tracking sensors; and
a processing circuitry configured to:
obtain a rotation center of a first one of the one or more spatial-tracking sensors, the first one of the one or more spatial-tracking sensors being disposed on a distal end of the telescope of the rigid endoscope, the telescope of the rigid endoscope being in a first pose,
obtain a first calibration based on the rotation center the first calibration being related to the first pose,
rotate, to a second pose, the telescope of the rigid endoscope relative to the camera head of the rigid endoscope,
obtain a second calibration, the second calibration being related to the second pose, and
select from the first calibration and the second calibration based upon a comparison of an error value between the first calibration and the second calibration,
wherein a second one of the one or more spatial-tracking sensors is disposed on the camera head, and
wherein the rotation of the telescope of the rigid endoscope relative to the camera head of the rigid endoscope is based upon a relative position of the first one of the one or more spatial-tracking sensors and the second one of the one or more spatial-tracking sensors.

2. The system according to claim 1, wherein each calibration of the calibration operation is a single-image calibration operation.

3. The system according to claim 1, wherein the calibration operation is initially performed a first time.

4. The system according to claim 3, wherein the calibration operation is performed a second time as an updated calibration operation.

5. The system according to claim 1, wherein at least one of the one or more spatial-tracking sensors is a rotary encoder.

6. The system according to claim 1, wherein the processing circuitry is further configured to estimate a rotation center of an image based upon the first pose and the second pose, the first pose and the second pose corresponding to principal points of the image.

7. The system according to claim 1, wherein the processing circuitry is further configured to update a camera matrix according to a direction of the rotation, the camera matrix being based upon a rotation angle, an image center, and the calibration operation.

8. A method of performing a calibration operation, comprising:
obtaining, via processing circuitry, a rotation center of a first one of one or more spatial-tracking sensors, the first one of the one or more spatial-tracking sensors being disposed on a distal end of a telescope of a rigid endoscope, the telescope of the rigid endoscope being in a first pose;
obtaining, via the processing circuitry, a first calibration based on the rotation center, the first calibration relating to the first pose;
rotating, to a second pose, the telescope of the rigid endoscope relative to a camera head of the rigid endoscope;
obtaining, via the processing circuitry, a second calibration, the second calibration relating to the second pose; and
selecting, via the processing circuitry, from the first calibration and the second calibration based upon a comparison of an error value between the first calibration and the second calibration,
wherein a second one of the one or more spatial-tracking sensors is disposed on the camera head of the rigid endoscope, and
wherein the rotation of the telescope of the rigid endoscope relative to the camera head of the rigid endoscope is based upon a relative position of the first one of the one or more spatial-tracking sensors and the second one of the one or more spatial-tracking sensors.

9. The method according to claim 8, wherein each calibration of the calibration operation is a single-image calibration operation.

10. The method according to claim 8, wherein the calibration operation is initially performed a first time.

11. The method according to claim 10, wherein the calibration operation is performed a second time as an updated calibration operation.

12. The method according to claim 8, wherein at least one of the one or more spatial-tracking sensors is a rotary encoder.

13. The method according to claim 8, further comprising estimating, via the processing circuitry, a rotation center of an image based upon the first pose and the second pose, the first pose and the second pose corresponding to principal points of the image.

14. The method according to claim 8, further comprising updating, via the processing circuitry, a camera matrix according to a direction of the rotation, the camera matrix being based upon a rotation angle, an image center, and the calibration operation.

15. A non-transitory computer-readable storage medium storing computer-readable instructions that, when executed by a computer having a processing circuitry, cause the computer to perform a calibration operation, the calibration operation comprising:
obtaining a rotation center of a first one of one or more spatial-tracking sensors, the first one of the one or more spatial-tracking sensors being disposed on a distal end of a telescope of a rigid endoscope, the telescope of the rigid endoscope being in a first pose;
obtaining a first calibration based on the rotation center, the first calibration relating to the first pose;
obtaining a second calibration, the second calibration relating to a second pose; and
selecting from the first calibration and the second calibration based upon a comparison of an error value between the first calibration and the second calibration,
wherein the second pose is achieved by rotating the telescope of the rigid endoscope relative to a camera head of the rigid endoscope,
wherein a second one of the one or more spatial-tracking sensors is disposed on the camera head of the rigid endoscope, and
wherein the rotation of the telescope of the rigid endoscope relative to the camera head of the rigid endoscope is based upon a relative position of the first one of the one or more spatial-tracking sensors and the second one of the one or more spatial-tracking sensors.

16. The non-transitory computer-readable storage medium according to claim 15, wherein each calibration of the calibration operation is a single-image calibration operation.

17. The non-transitory computer-readable storage medium according to claim 15, wherein the calibration operation is initially performed a first time.

18. The non-transitory computer-readable storage medium according to claim 17, wherein the calibration operation is performed a second time as an updated calibration operation.

19. The non-transitory computer-readable storage medium according to claim 15, further comprising estimating a rotation center of an image based upon the first pose and the second pose, the first pose and the second pose corresponding to principal points of the image.

20. The non-transitory computer-readable storage medium according to claim 15, further comprising updating a camera matrix according to a direction of the rotation, the camera matrix being based upon a rotation angle, an image center, and the calibration operation.

\* \* \* \* \*